(12) United States Patent
Friedman et al.

(10) Patent No.: US 11,291,761 B2
(45) Date of Patent: *Apr. 5, 2022

(54) SYSTEM OF MEDICAL INDICATORS HAVING MULTISENSORY, MULTIPURPOSE AND MULTIFUNCTIONAL FEATURES

(71) Applicant: Star Luminal LLC, San Antonio, TX (US)

(72) Inventors: David J. Friedman, San Antonio, TX (US); Elizabeth S. Friedman, San Antonio, TX (US); Daniel O. Hogenauer, Kennett Square, PA (US); Eric A. Haddad, Boerne, TX (US); Bryce G. Rutter, St. Louis, MO (US); Max W. Ryan, St. Louis, MO (US); Tucker P. Brown, St. Louis, MO (US)

(73) Assignee: Star Luminal LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/529,441

(22) Filed: Aug. 1, 2019

(65) Prior Publication Data
US 2020/0069866 A1 Mar. 5, 2020

Related U.S. Application Data

(60) Provisional application No. 62/724,424, filed on Aug. 29, 2018.

(51) Int. Cl.
*A61M 39/08* (2006.01)
*A61M 5/14* (2006.01)

(52) U.S. Cl.
CPC ........ *A61M 5/1409* (2013.01); *A61M 5/1411* (2013.01); *A61M 39/08* (2013.01); *A61M 2205/60* (2013.01)

(58) Field of Classification Search
CPC .. A61M 5/1409; A61M 5/1411; A61M 39/08; A61M 2205/60; G09F 3/205
See application file for complete search history.

(56) References Cited

U.S. PATENT DOCUMENTS 3,755,921 A * 9/1973 Heller ................ G09B 19/003
434/322
5,115,586 A * 5/1992 Hawker ............. G02B 6/4482
40/316

(Continued)

FOREIGN PATENT DOCUMENTS

WO 2006/083933 A1 8/2006

OTHER PUBLICATIONS

International Search Report and Written Opinion issued by the European Patent Office dated Nov. 6, 2019 in International Application No. PCT/US2019/044711.

(Continued)

*Primary Examiner* — Cassandra Davis
(74) *Attorney, Agent, or Firm* — Greenberg Traurig, LLP

(57) ABSTRACT

An indicator includes a body having a first end, a second end opposite the first end, a first surface and a second surface opposite the first surface, each of which extends from the first end to the second end, and an aperture extending from the first end to the second end, the aperture being sized and shaped to receive a tube, and at least one of the first and second surfaces including a haptic signature formed thereon.

11 Claims, 25 Drawing Sheets

(56) References Cited

U.S. PATENT DOCUMENTS

| | | | | |
|---|---|---|---|---|
| 5,334,955 | A | * | 8/1994 | Strnad .................. H03H 1/0007 |
| | | | | 333/12 |
| 5,367,809 | A | * | 11/1994 | Ross ........................ G09F 3/12 |
| | | | | 24/DIG. 29 |
| 5,896,826 | A | * | 4/1999 | Winer ....................... G09F 3/04 |
| | | | | 116/200 |
| 6,050,824 | A | * | 4/2000 | Stuart ..................... G09B 17/00 |
| | | | | 434/112 |
| 6,059,768 | A | | 5/2000 | Friedman |
| 6,335,672 | B1 | * | 1/2002 | Tumlin ................... H01F 17/06 |
| | | | | 336/175 |
| 6,613,012 | B2 | | 9/2003 | Kraushaar |
| 6,823,617 | B2 | * | 11/2004 | Schweikert ......... A61M 39/284 |
| | | | | 40/299.01 |
| 7,322,135 | B2 | * | 1/2008 | Gulati ..................... A61B 7/02 |
| | | | | 181/131 |
| 7,331,130 | B2 | | 2/2008 | Schweikert |
| 7,338,476 | B2 | | 3/2008 | Kraushaar |
| 7,374,318 | B2 | | 5/2008 | Brooks et al. |
| 7,455,662 | B2 | | 11/2008 | Kraushaar |
| D610,482 | S | * | 2/2010 | Shaw ............................ D11/81 |
| 7,758,565 | B2 | | 7/2010 | Melsheimer |
| 8,151,497 | B2 | | 4/2012 | Wieieke |
| 8,327,843 | B2 | | 12/2012 | Warden et al. |
| 8,516,727 | B1 | * | 8/2013 | Maraia .................... G09F 3/205 |
| | | | | 40/316 |
| 8,597,254 | B1 | | 12/2013 | Mullet et al. |
| 8,752,314 | B2 | | 6/2014 | Schweikert |
| 8,882,718 | B2 | | 11/2014 | Mullet et al. |
| 9,308,328 | B2 | | 4/2016 | Kawamura et al. |
| 9,775,779 | B2 | * | 10/2017 | Ali ........................ A61J 1/1412 |
| 9,775,950 | B2 | | 10/2017 | Creaturo |
| 9,779,428 | B2 | | 10/2017 | Wieneke |
| 9,799,428 | B2 | | 10/2017 | Wieneke |
| 9,833,560 | B2 | | 12/2017 | Reichert et al. |
| 9,919,095 | B2 | | 3/2018 | Reichert et al. |
| 9,925,329 | B2 | | 3/2018 | Reichert et al. |
| 10,019,916 | B2 | | 7/2018 | Muraco et al. |
| 10,207,056 | B2 | | 2/2019 | Avery et al. |
| 10,286,150 | B2 | | 5/2019 | Harms et al. |
| D913,150 | S | * | 3/2021 | Tomlinson .................. D11/200 |
| 2002/0058928 | A1 | * | 5/2002 | Antonio, II ......... A61M 5/1407 |
| | | | | 604/523 |
| 2005/0171492 | A1 | * | 8/2005 | Rodriquez ............ A61M 39/08 |
| | | | | 604/264 |
| 2005/0267404 | A1 | * | 12/2005 | Kraushaar ............... A61M 5/14 |
| | | | | 604/80 |
| 2006/0104910 | A1 | | 5/2006 | Lerner |
| 2006/0118507 | A1 | * | 6/2006 | Feldman ............ B65D 23/0871 |
| | | | | 215/12.1 |
| 2006/0127863 | A1 | * | 6/2006 | Avery ..................... G09B 1/32 |
| | | | | 434/112 |
| 2007/0219510 | A1 | | 9/2007 | Zinn et al. |
| 2009/0255954 | A1 | * | 10/2009 | Raja ....................... A47G 19/24 |
| | | | | 222/23 |
| 2012/0186116 | A1 | * | 7/2012 | Ohnishi ................ G09F 3/0295 |
| | | | | 40/316 |
| 2012/0260543 | A1 | * | 10/2012 | Dunn ......................... G09F 3/06 |
| | | | | 40/316 |
| 2012/0285366 | A1 | * | 11/2012 | Perez .................... B65D 25/205 |
| | | | | 116/278 |
| 2013/0263482 | A1 | * | 10/2013 | Strater ..................... G09F 3/205 |
| | | | | 40/316 |
| 2014/0082980 | A1 | | 3/2014 | Sherman et al. |
| 2014/0100533 | A1 | | 4/2014 | Lyons |
| 2015/0238697 | A1 | | 8/2015 | Michaud et al. |
| 2015/0262515 | A1 | | 9/2015 | Leonardis et al. |
| 2017/0110035 | A1 | | 4/2017 | Weglarz et al. |
| 2020/0046945 | A1 | * | 2/2020 | Vera ....................... A61M 25/02 |

OTHER PUBLICATIONS

Needleman, Sarah E., "Life Ahead of the Curve—Fast Forward", The Future of Everything, The Wall Street Journal, May 2018, pp. 7-10.

* cited by examiner

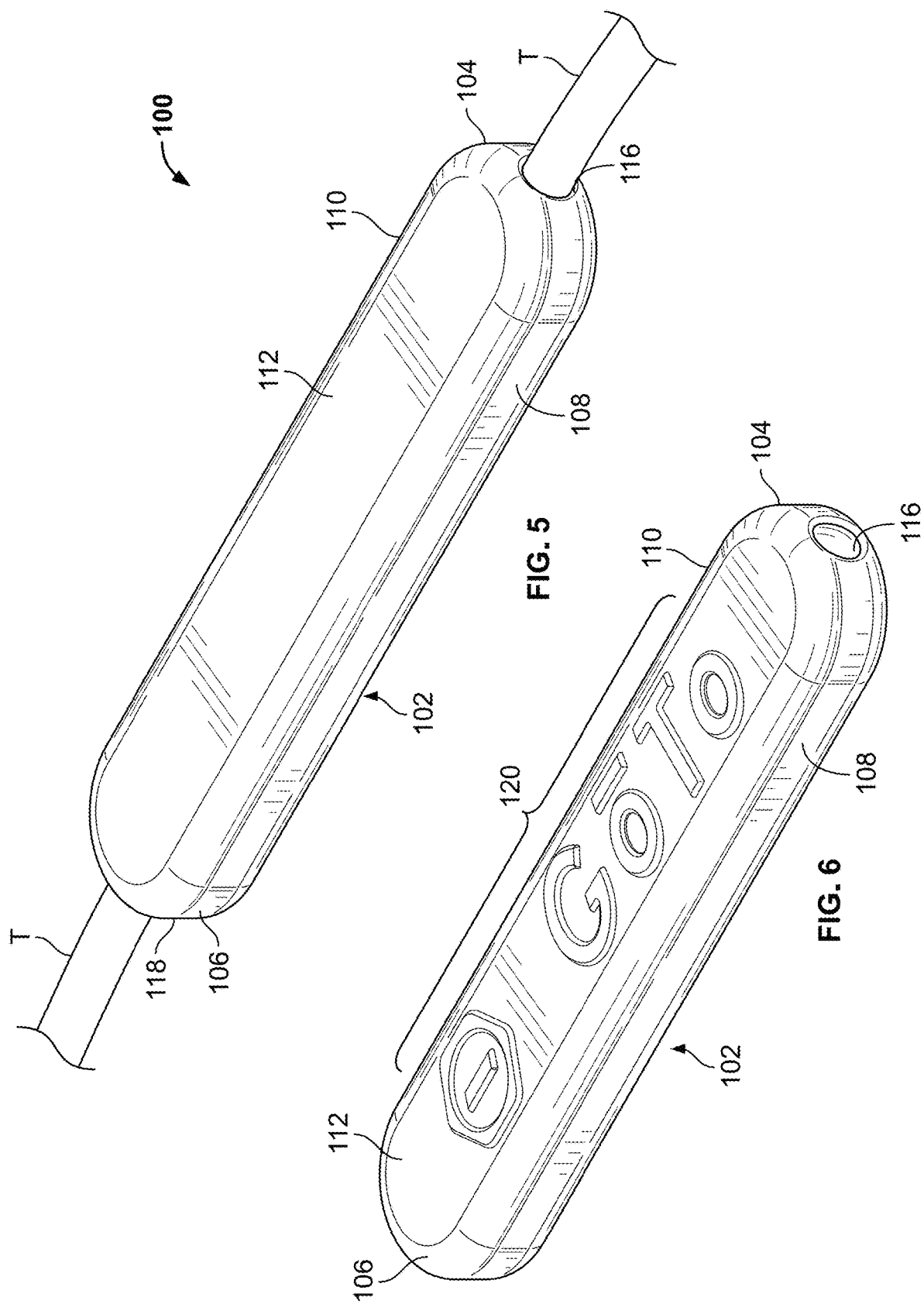

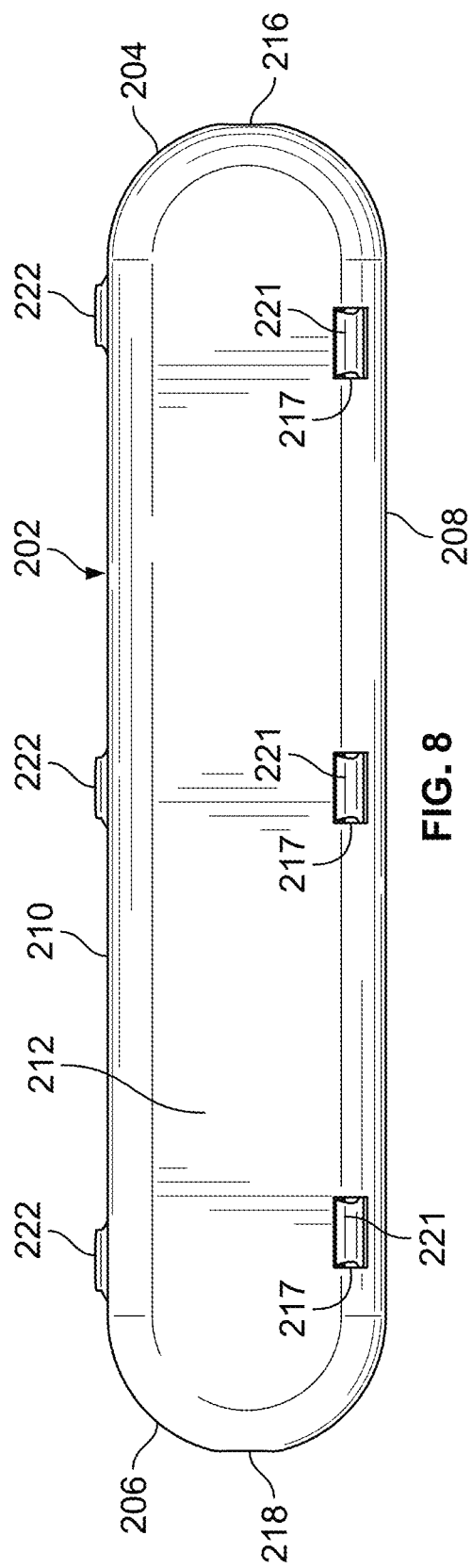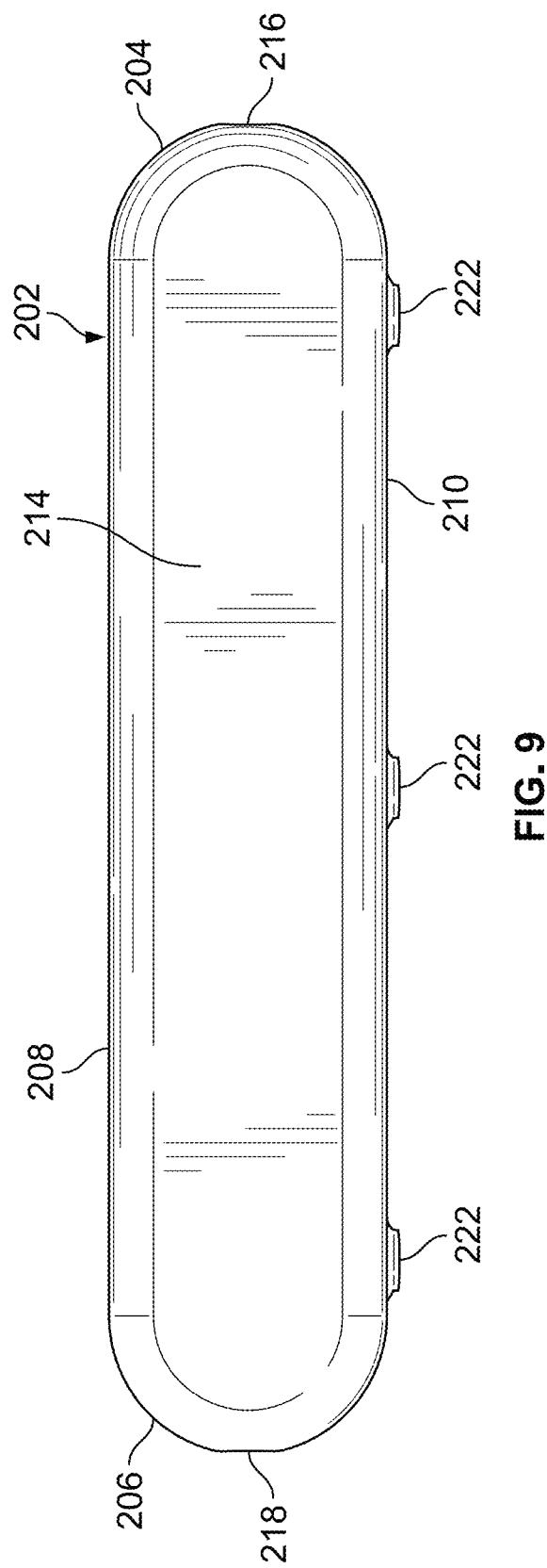

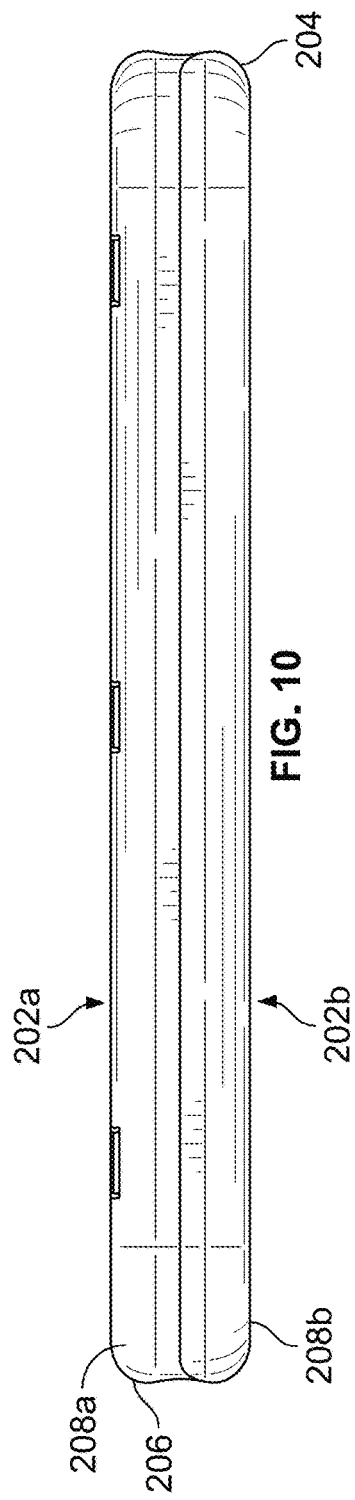
FIG. 10
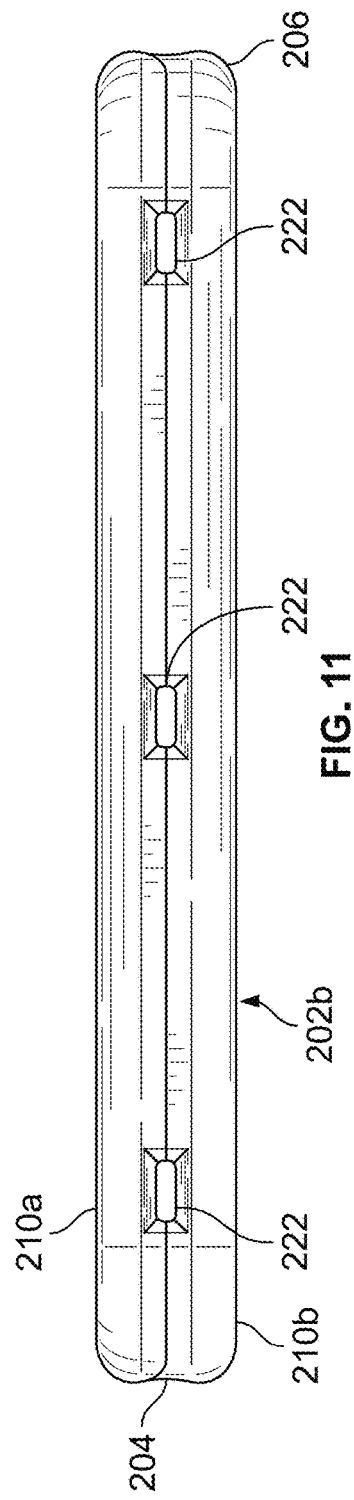
FIG. 11
FIG. 13
FIG. 12

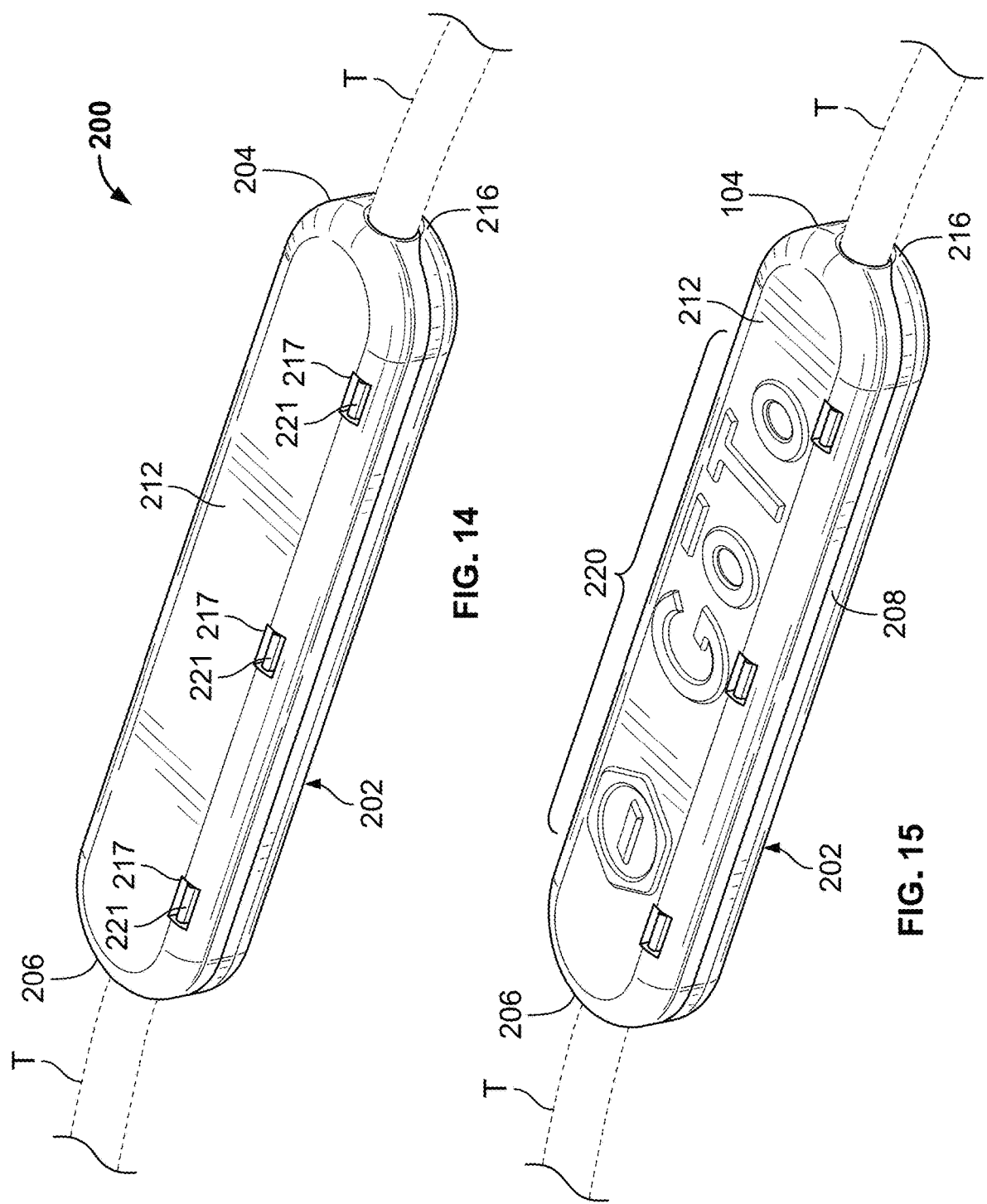

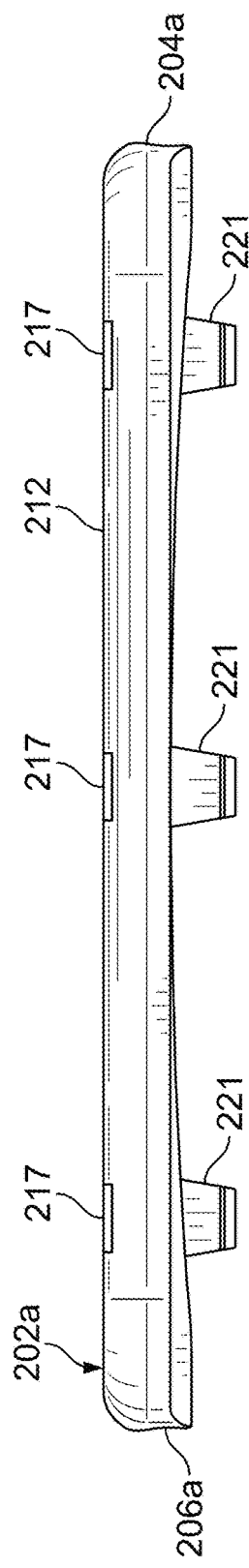
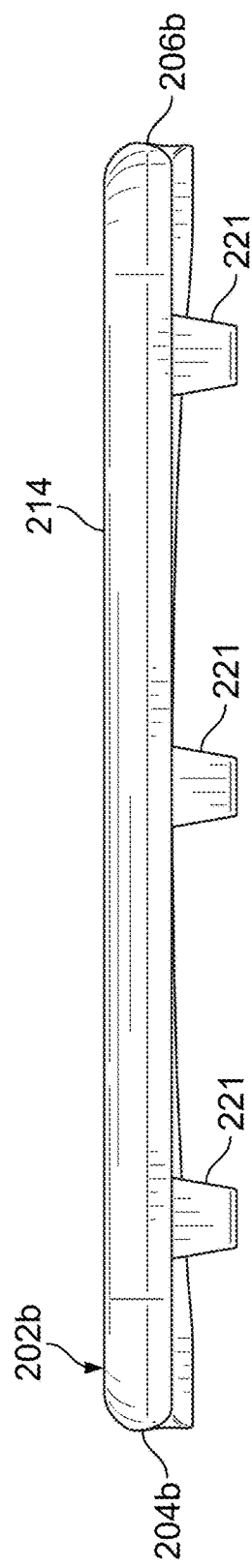
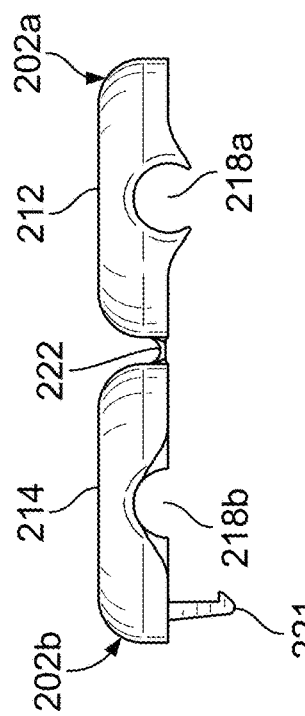
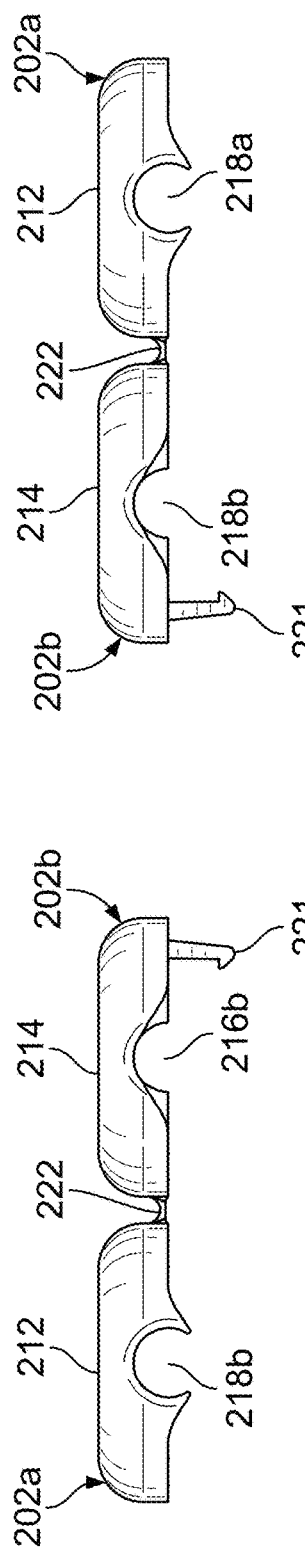

SYSTEM OF MEDICAL INDICATORS HAVING MULTISENSORY, MULTIPURPOSE AND MULTIFUNCTIONAL FEATURES

CROSS-REFERENCE TO RELATED APPLICATION

This application is a Section 111(a) application relating to and claiming the benefit of commonly-owned, U.S. Provisional Patent Application No. 62/724,424, titled "ADMINISTRATION OF MEDICAMENTS THROUGH INTRAVENOUS TUBING USING MULTISENSORY FEATURES AND OTHER INDICATORS—A SYSTEM TO REDUCE MEDICATION ERRORS AND INFORM PATIENTS," having a filing date of Aug. 29, 2018, which is incorporated by reference herein in its entirety.

FIELD OF THE INVENTION

The present invention relates to indicators for labelling and identifying intravenous ("IV") tubing, and the contents thereof, using sensory stimuli, such as visual and haptic (i.e., tactile; pertaining to the sensation of touch) signatures and other identifiers.

BACKGROUND

Literature suggests that medical errors constitute the third highest cause of death in the United States. Among medical errors, human medication errors rank first. By reducing human error in the administration of intravenous medication/fluid, more than 7,000 lives might be saved each year, and a similar volume of medication-related patient complications may be avoided.

What is needed is a system that reduces medical errors by (1) providing a mechanism(s) to limit medical errors during a medical crisis; (2) identifying a "safe-line" for medical personnel to use in a medical emergency; (3) creating patient, patient family or advocate awareness of therapy; (4) allowing quick, cognitive recognition of medical care at medical shift change; (5) enumerating the number of different medications/fluids in use or that have been administered; and (6) avoiding the inadvertent administration of therapy in a non-intravenous line (e.g., a spinal line or an arterial line rather than a venous line).

Tubing used for infusion is generic, clear and indistinguishable from other lines in use regardless of the tubing's contents. The tubing is part of an intravenous (IV) line. This line is also known as an infusion set, IV set, infusion line, or simply "the line". IV fluids are administered through a thin, flexible transparent plastic tube. The IV tube line connects to the bag of IV solution. This line is used to infuse, continuously or intermittently, fluids or medication. It includes the following: (1) a spike and drip chamber which attaches to the bag of fluid; (2) backcheck valve which prevents fluid or medication from travelling up the line; (3) access ports, which are used to infuse secondary medications and give push medications; and (4) a roller clamp, which is used to regulate the speed of, or to stop or start, a gravity infusion. The number of lines needed for infusion therapy depends on the medical condition of the patient and how acutely ill the patient is at the time.

SUMMARY OF THE INVENTION

The exemplary embodiments present a novel method to avoid and reduce the probability of medication errors in patients receiving IV therapy.

The exemplary embodiments provide a mechanism for the rapid and repeated identification of the correct IV line to use in an emergency situation. In a medical crisis, care is often chaotic and multiple lines may be needed or are already in use. When an emergency medication is needed, safe, fast, and confident delivery of the medication through the correct, existing IV line(s) is essential. The correct IV line must carry a fluid which is compatible with all emergency medications and the correct IV line must be frequently recognized for repeated use, if needed.

The exemplary embodiments provide a "safe-line" or "tag" on an appropriate line that facilitates rapid identification of a "safe" line to use in the emergency. Such a critical situation routinely arises during aeromedical and ground medical transport, but can likewise happen in a pre-hospital (e.g., ambulance or medical airlift) or hospital environment.

The exemplary embodiments further provide the application of a specific label on the line to denote the medication in use. This provides a unique ability for both the caregivers, the patient (self-care), as well as patient's advocate or family in attendance, to become informed of the medication in use. This also provides critical information regarding the initiation, duration and cessation of the medication for the patient. It confirms patient and family expectations regarding information they have been told about current and future treatment. It provides an additional check on the therapy as well as to avoid errors by caregivers.

The exemplary embodiments provide immediate cognitive awareness at shift change in a pre-hospital or hospital environment. This also applies with the entry of medical personnel into the patient's room whether they are familiar with the patient, or not. This information is important since changes in patient care may have occurred in the interim since the patient was last seen or examined either by a nurse or physician (e.g., initiation of anticoagulation in a patient expected to go for surgery). Furthermore, there may have been a lack of communication regarding these changes (or information missed because of the complexity of, or deficiency in, the medical record). This immediate cognitive awareness is particularly important in an academic environment where trainee caregivers are in abundance and the risks of medical errors are higher.

The exemplary embodiments provide an identification system that embodies a mechanism for the enumeration of the number of medication(s) in use (e.g., multiple medications of the same class). In so doing this additionally allows for the awareness of either the deterioration or improvement in the patient's condition for both caregiver, patient and family. This would be the case such as when the number of pressor (blood pressure medication) tags are increased or decreased respectively. Finally, the numerical ability of the blood transfusion tag allows for the tabulation of the number of units of the blood product infused as well as confirmation of the patient's blood type.

The exemplary embodiments assist in the prevention of the administration of certain medications into an inappropriate line that may result in catastrophic morbidity or death (e.g., vincristine chemotherapy given intrathecally). Just as it is important for the content of an IV line to be easily identified by caregivers, so it is of critical importance for an incorrect line to be readily recognizable to avoid an administration error.

In an embodiment, an indicator includes a body having a first end, a second end opposite the first end, a first surface and a second surface opposite the first surface, each of which extends from the first end to the second end, and an aperture extending from the first end to the second end, the aperture being sized and shaped to receive a tube, and at least one of the first and second surfaces including a haptic signature formed thereon.

In an embodiment, the haptic signature is embossed on the at least one of the first and second surfaces. In an embodiment, the haptic signature includes a height in a range of 0.02 inch and 0.08 inch.

In an embodiment, the haptic signature is debossed on the at least one of the first and second surfaces. In an embodiment, the haptic signature includes depth in a range of 0.02 inch to 0.08 inch.

In an embodiment, the haptic signature includes a plurality of indicia elements spaced apart from one another. In an embodiment, a spacing between an adjacent pair of the plurality of indicia elements is in a range of 0.02 inch to 0.08 inch. In an embodiment, the plurality of indicia elements includes a series of elements having similar shapes, each of the series of elements includes a height that varies from the height of another of the series of elements. In an embodiment, each of the heights of the series of elements of the plurality of indicia elements is in a range of 0.005 inch to 0.08 inch.

In an embodiment, the haptic signature includes a textured portion having a grainy texture. In an embodiment, the textured portion includes a plurality of grains having sizes in a range of about 0.005 inch to about 0.010 inch.

In an embodiment, the haptic signature includes a first end, a second end opposite the first end of the haptic signature, and a width that varies along a length extending from the first and second ends of the haptic signature, wherein the width varies within a range of 0.05 inch to 0.5 inch.

In an embodiment, the haptic signature includes an embossed portion and a debossed portion, wherein the embossed portion includes a height in a range of 0.02 inch and 0.08 inch, and debossed portion includes a depth in a range of 0.02 inch to 0.08 inch.

In an embodiment, the haptic signature includes an embossed portion and a debossed portion that is debossed within the embossed portion, wherein the embossed portion includes a height in a range of 0.02 inch and 0.08 inch, and the debossed portion includes a depth in a range of 0.02 inch to 0.08 inch.

In an embodiment, the body includes a first member and a second member connected movably to the first member, wherein each of the first and second members includes an interior surface and a channel formed within the interior surface and extending from a first end thereof to a second end thereof, wherein the first and second members are movable between an open position and closed position, and wherein the channels of each of the first and second members form the aperture when the first and second members are in their closed position.

In an embodiment, the first member of the body includes at least one tab extending from the interior surface thereof, and the second member of the body includes at least one groove formed within the interior surface thereof, and wherein the at least one tab is sized and shaped to engage removably the at least one groove. In an embodiment, the body includes at least one hinge connected to the first and second members.

In an embodiment, the body includes a plurality of removable tabs.

In an embodiment, the tube is an intravenous tube and the haptic signature corresponds to a medication delivered by the intravenous tube.

In an embodiment, a combination includes at least one intravenous tube and a plurality of indicators, each indicator comprising a body having a first end, a second end opposite the first end, a first surface and a second surface opposite the first surface, each of which extends from the first end to the second end, and an aperture extending from the first end to the second end, the aperture being sized and shaped to receive the at least one intravenous tube, and at least one of the first and second surfaces including a haptic signature formed thereon, the haptic signature corresponding to a medication delivered by the at least one intravenous tube.

In an embodiment, the haptic signature of a first one of the plurality of indicators is different from the haptic signature of a second one of the plurality of indicators.

In an embodiment, the haptic signature of each of the plurality of indicators is different from the haptic signature of others of the plurality of indicators.

In an embodiment, the at least one intravenous tube includes a plurality of intravenous tubes, and the haptic signature of the first one of the plurality of indicators corresponds to a medication delivered by a first one of the plurality of intravenous tubes, and the haptic signature of the second of the plurality of indicators corresponds to another medication delivered by a second one of the plurality of intravenous tubes.

In an embodiment, the haptic signature of each of at least two of the plurality of indicators are identical to one another. In an embodiment, the haptic signature of each of at least three of the plurality of indicators are identical to one another.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 5 is a top perspective view thereof, with the indicator being attached to tubing;

FIG. 6 is a top perspective view thereof, with the indicator including a haptic signature on a surface thereof;

FIG. 8 is a top plan view thereof;

FIG. 9 is a bottom plan view thereof;

FIG. 10 is a front elevational view thereof;

FIG. 11 is a rear elevational view thereof;

FIG. 12 is a left side elevational view thereof;

FIG. 13 is a right side elevational view thereof;

FIG. 14 is a top perspective view thereof, with the indicator being attached to tubing;

FIG. 15 is a top perspective view thereof, with the indicator including a haptic signature on a surface thereof;

FIG. 19 is a front elevational view thereof;

FIG. 20 is a rear elevational view thereof;

FIG. 21 is a left side elevational view thereof;

FIG. 22 is a right side elevational view thereof;

DETAILED DESCRIPTION OF THE DRAWINGS

Figure 1:
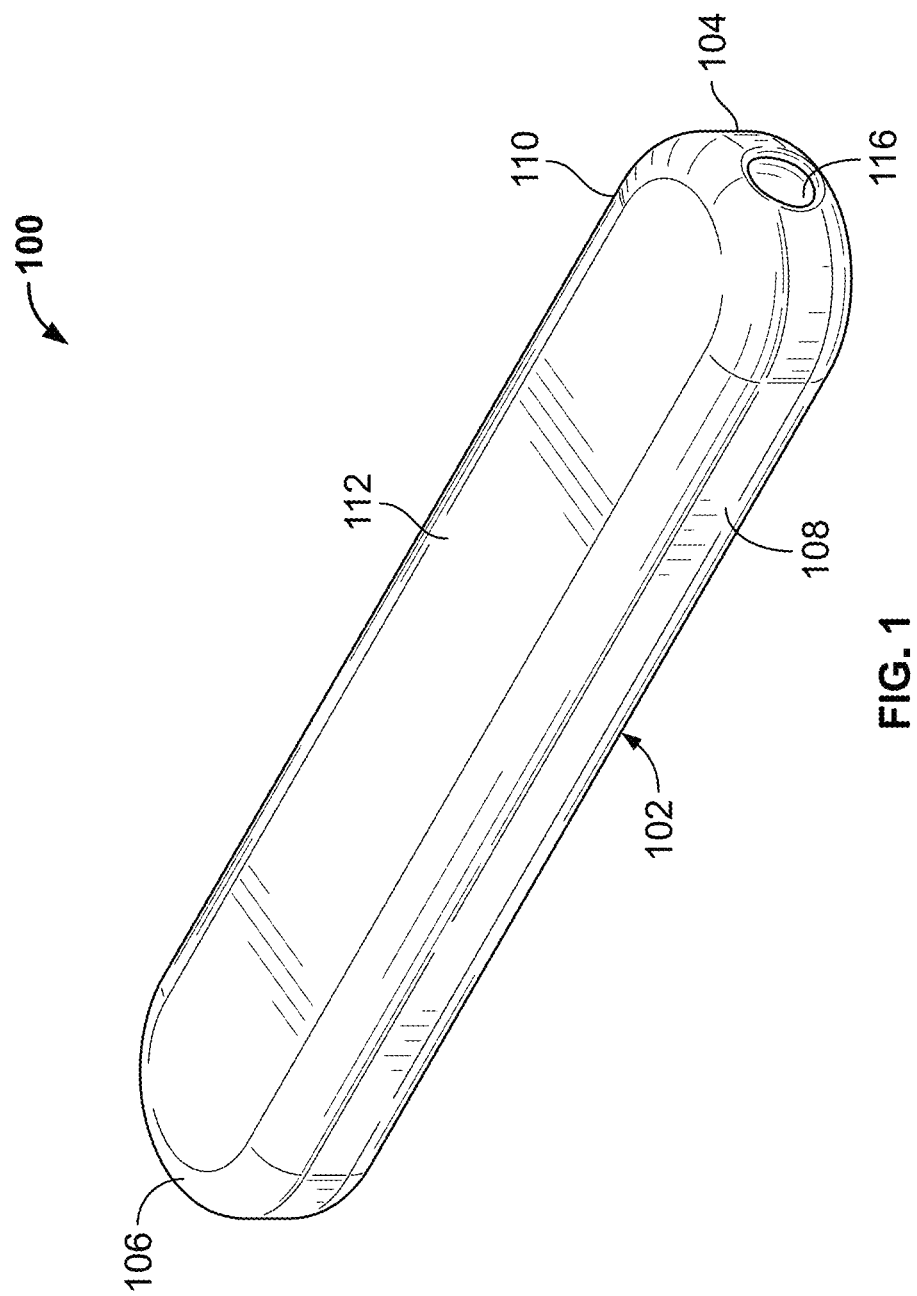
FIG. 1 is a top perspective view of an embodiment of an intravenous tubing indicator.
Figure 2:
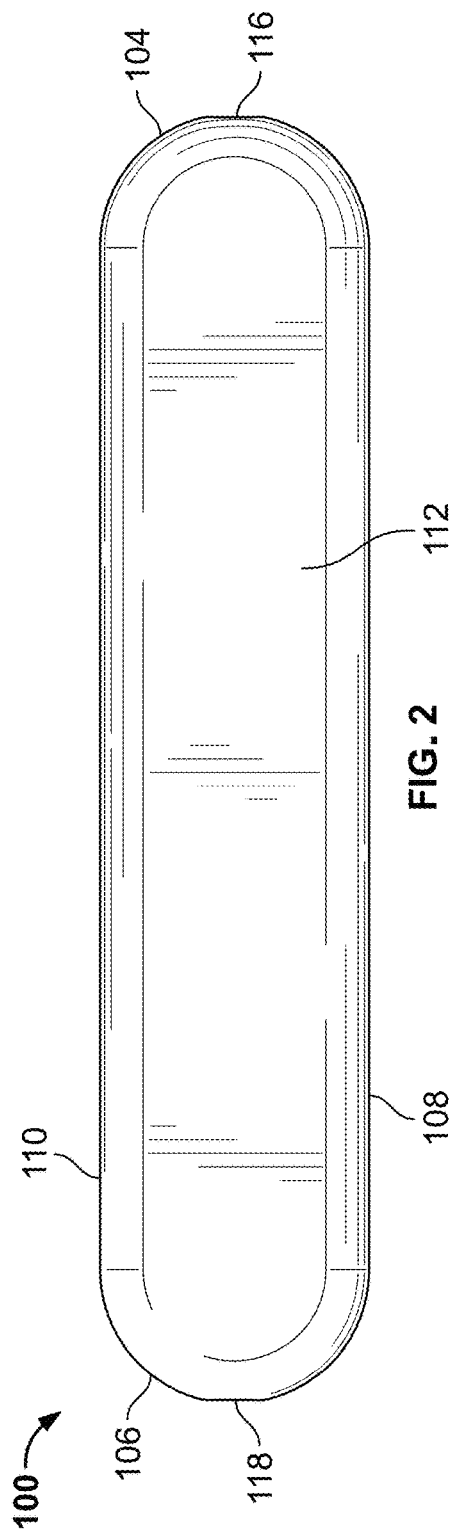
FIG. 2 is top plan view thereof, the bottom plan view being a mirror image thereto.
Figure 3:
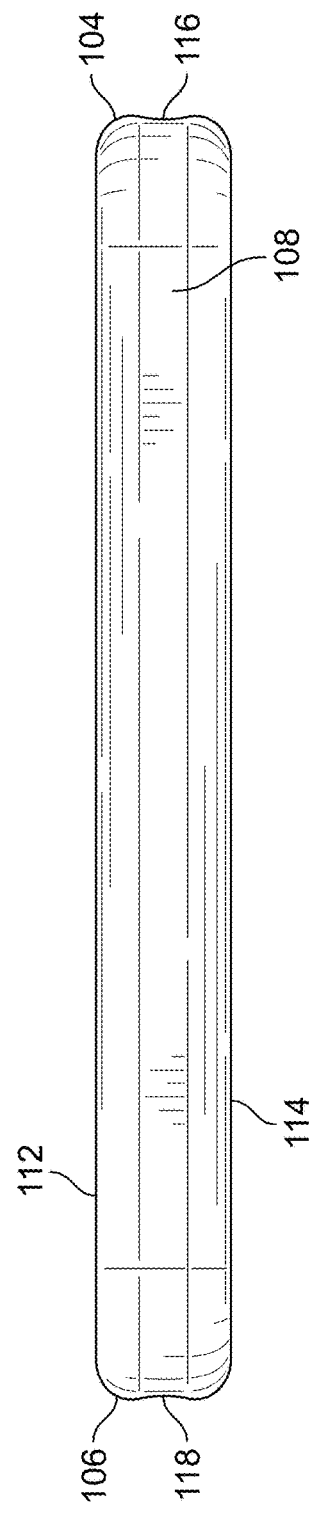
FIG. 3 is a front elevation view thereof, the rear elevational view being a mirror image thereto.
Figure 4:
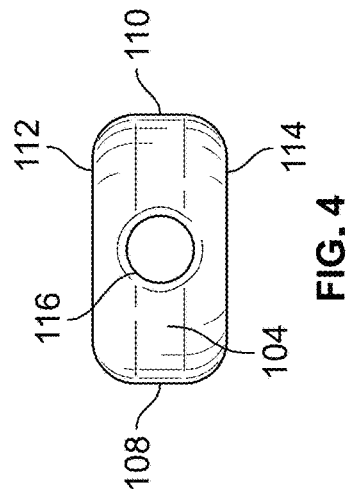
FIG. 4 is a left side elevational view thereof, the right side elevational view being a mirror image thereof.
Figure 7:
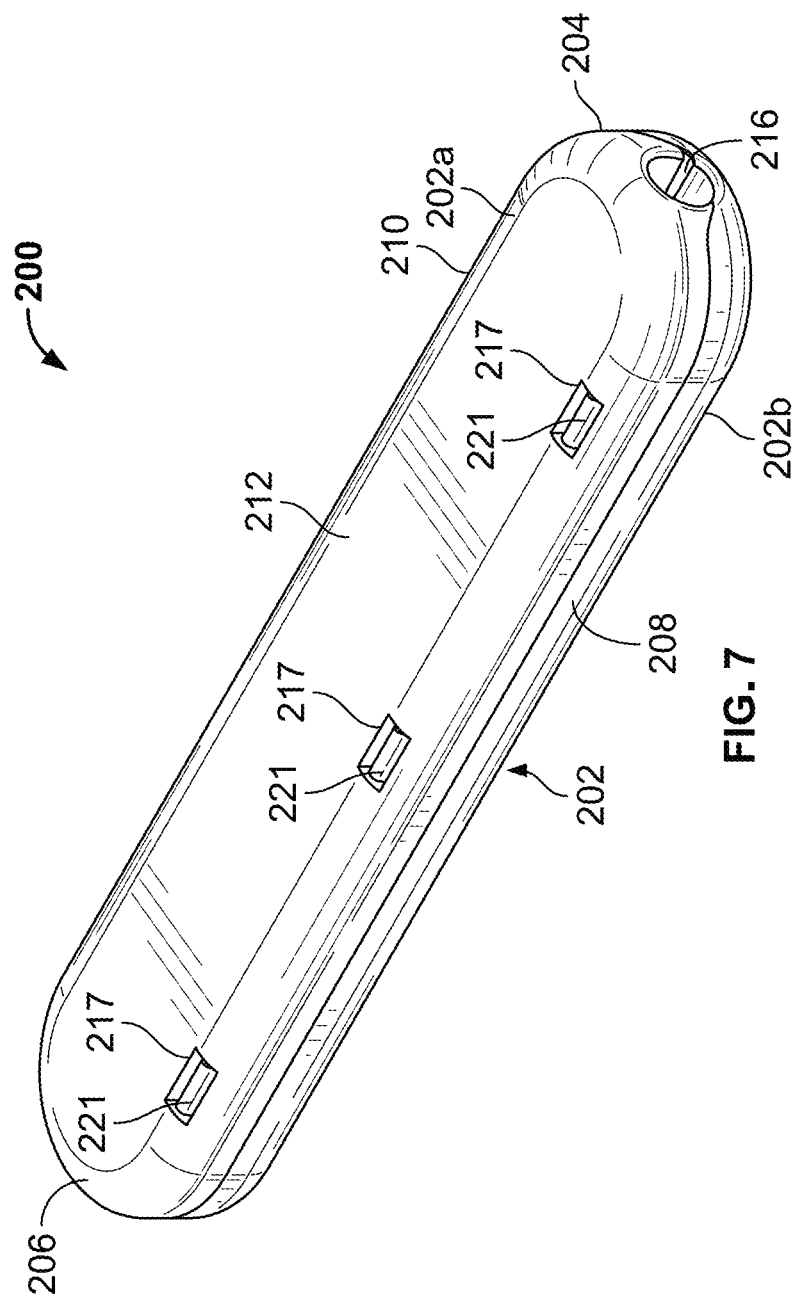
FIG. 7 is a top perspective view of another embodiment of an intravenous tubing indicator in a closed position.
Figure 16:
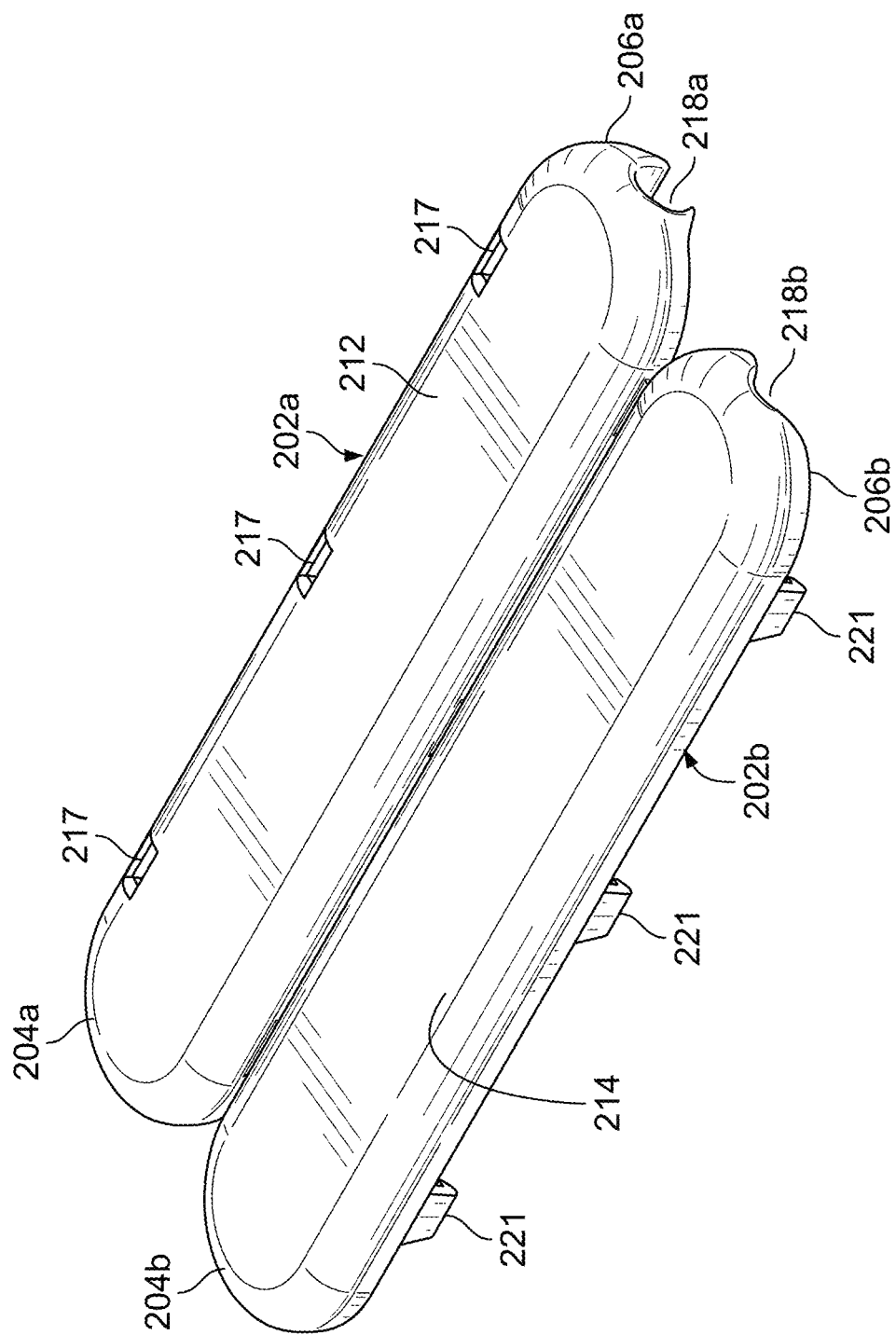
FIG. 16 is a top perspective view of the intravenous tubing indicator of FIG. 7 but in an open position.
Figure 17:
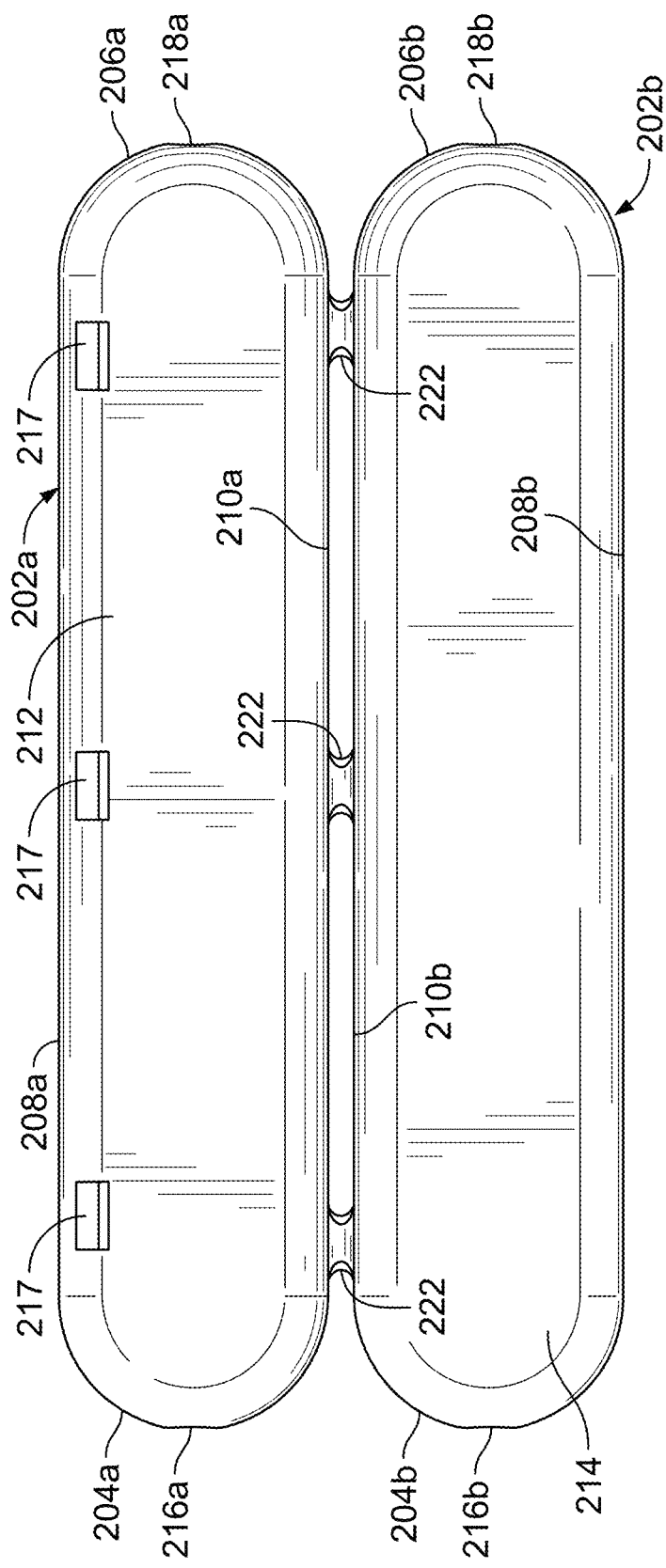
FIG. 17 is a top plan view thereof.
Figure 18:
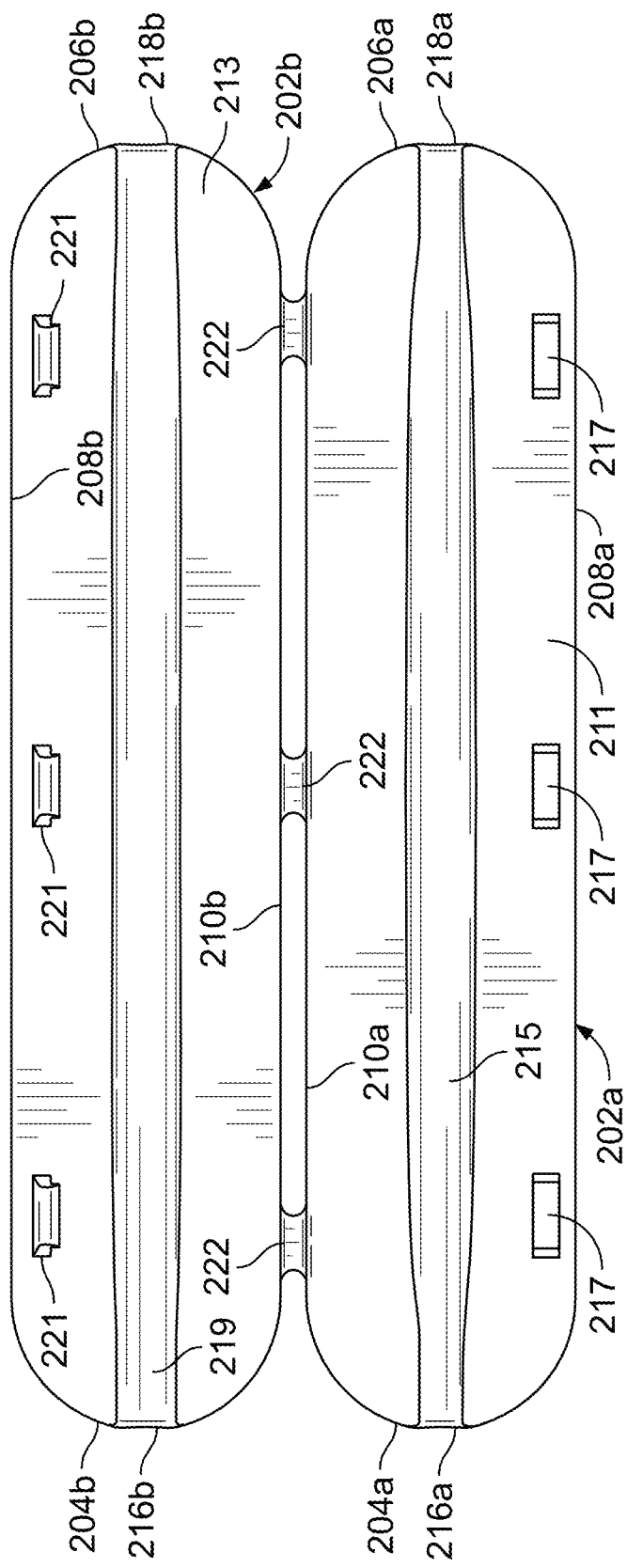
FIG. 18 is a bottom plan view thereof.

Multiple intravenous (IV) tubing indicators (sometimes referred to herein as "tags") are disclosed. Such indicators are affixed to intravenous tubing in a hospital or other medical environment. These function to provide to caregivers and patients more efficient, reliable and accurate identification of medications or other substances being conveyed to the patient via the IV tubing.

In some embodiments, the intravenous tubing indicators are haptic (i.e., tactile; pertaining to the sensation of touch). This assists with recognition of the indicator and, thereby, the medication, by feel, as well as in conditions of low light. In some embodiments, the indicators are fabricated to convey multi-sensory communications to a user (e.g., a physician, nurse, or other medical personnel treating a patient) to provide further recognition regarding the medication or other substances contained in the intravenous tubing. In some embodiments, the multi-sensory communication may include symbols, print/text, color, shape, luminosity (e.g., generated by a luminescent) and/or touch/tactile stimuli. Specific combinations of multi-sensory communications correspond and alert the caregivers to different classes or types of medication or fluids. This reminds or warns the user of the contents of the intravenous tubing, in order to take appropriate action in connection therewith, should this be necessary (e.g., the insulin tag has a grainy feel/texture resembling sugar). Use of the intravenous tubing indicators thereby minimizes or prevents medication-related errors that can be catastrophic, and even fatal, to the patient.

In some embodiments, the indicators include a system of IV-line tags with haptic signatures for the use of differentiating medications or fluids through various sensory modalities including visual symbols, luminosity, print/text, color, textures, luminosity and touch. Each distinct haptic signature is located on its own tag that is configured to be placed on multiple locations of the IV tubing to prevent IV-line mix-ups and errors.

In some embodiments, the indicators are plastic tags that are secured to the IV line. In some embodiments, the plastic tags are injection molded. In some embodiments, the tags are clip-on tags (that cannot be removed). In some embodiments, one or more separate clips is/are used to attach the tags to the IV line. In some embodiments, the clips are removable. In some embodiments, a face of the tag includes a centralized haptic signature that fits the thumb of a user. In some embodiments, an outer ring surrounding the haptic signature includes a label at the top and pull/twist off indicators on each side that numerically indicate the number of similar lines (or class of drug) in use. In some embodiments, a back of the tag includes two snap-on features that allow for easy connection to IV tubing. In some embodiments, the haptic tags are sized so as to fit the fingers of most males and most females. In some embodiments, the haptic tags are sized so as to fit different finger sizes within a range spanning, at the smallest end, the 5th percentile of female fingers and, at the largest end, the 95th percentile of male fingers. In one embodiment, the haptic tags are approximately 2 inches tall by 1.5 inches wide, which is a size that accounts for the 5th percentile female fingers and the 95th percentile male fingers.

The indicators (e.g. tags) allow medical personnel to easily locate and identify IV-lines through their corresponding haptic signatures and visual cues. Tags closer to the patient allow for quick and easy identification. A user may identify a specific tag through a range of sensory modalities including color, label, luminosity, symbol, or texture. The haptic signature is positioned so that a user's thumb can easily "read" with natural thumb flexion while still being able to see the label and color associated with the tag.

In various embodiments, an individual tag includes a color, label, and a specific haptic signature to identify the drug with which it is associated. Haptic signatures include textures, icons, and metaphors that are meaningful and familiar to clinical professionals (e.g. grainy feel/texture resembling sugar for insulin line; prickly feel/texture for narcotic lines; wavy feel/texture for anticoagulants) To differentiate shapes and prevent confusion between tags, haptic signatures may include varying heights, spacing, textures, degrees of roughness, and/or sizes in various embodiments.

In some embodiments, each tag (except for insulin) includes sequentially numbered pull/twist-off tabs to indicate the number of IV bags a patient has used in a day. The insulin tag should not include any pull/twist-off tabs to prevent confusion and overdosing (see FIG. 37). Blood transfusion lines have different tabs (see FIG. 34 that allow medical personnel to indicate the blood type of the patient as well as how many transfusions they have received in a day (e.g., by removing one tab at the time of each transfusion, by removing a quantity of tabs corresponding to the number of transfusions that have been received, etc.).

FIGS. 1-6 illustrate a first exemplary embodiment of an intravenous tubing indicator 100 according to the present disclosure. The indicator 100 includes a body 102 that is monolithically formed, and has two opposed ends 104, 106. Opposed sides 108, 110 extend between ends 104, 106. Opposed top and bottom surfaces 112, 114 extend between ends 104, 106 and are bordered by sides 108, 110. A central, longitudinal aperture extends through the body 102 from the end 104 to the end 106, such that the end 104 defines an aperture 116 therein, and the end 106 defines an aperture 118 therein. Apertures 116, 118 are dimensioned so as to receive a length of intravenous tubing T therethrough. More particularly, the intravenous tubing T is inserted through aperture 116, extended along the interior of the indicator body 102, and exits therefrom through aperture 118, as shown in FIG. 5.

At least one of the top or bottom surfaces 112, 114 on the indicator body 102 includes a haptic signature 120. The haptic signature 120 may include images, designs, numbers, letters, punctuation marks, patterns, other indicia, or any combination thereof (collectively "indicia"). The haptic signature 120 is formulated to convey to a user (e.g., a physician, nurse or other medical personnel treating a patient) the nature of the medication or other substance that is contained within the intravenous tubing T and being delivered to the patient thereby. The haptic signature 120 is formed on the surface(s) 112, 114 of the indicator body 102 by any means known in the art, such as, for example, embossing, 3D printing, engraving, or as part of the injection-molding process.

In some embodiments, at least one indicator 100 within a set of indicators includes a haptic signature 120 that is embossed on (i.e., raised from) the corresponding one of the surfaces 112, 114 of the indicator body 102. In some embodiments, such a haptic signature 120 is embossed to a height that is selected to enable a user to identify indicia in the haptic signature 120, and thereby to identify the medicament or other substance that is contained within the tubing T to which the indicator 100 is attached. In some embodiments, the embossing height is in a range of between 0.02 inch and 0.08 inch. In some embodiments, the embossing height is in a range of between 0.02 inch and 0.04 inch. In some embodiments, the embossing height is in a range of between 0.04 inch and 0.06 inch. In some embodiments, the embossing height is in a range of between 0.06 inch and 0.08 inch. In some embodiments, the embossing height is in a range of between 0.02 inch and 0.06 inch. In some embodiments, the embossing height is in a range of between 0.04 inch and 0.08 inch. In some embodiments, the embossing height is in a range of between 0.01 inch and 0.07 inch. In some embodiments, the embossing height is in a range of between 0.01 inch and 0.03 inch. In some embodiments, the embossing height is in a range of between 0.01 inch and 0.04 inch. In some embodiments, the embossing height is in a range of between 0.01 inch and 0.05 inch. In some embodiments, the embossing height is in a range of between 0.01 inch and 0.06 inch. In some embodiments, the embossing height is in a range of between 0.05 inch and 0.07 inch. In some embodiments, the embossing height is in a range of between 0.01 inch and 0.08 inch. In some embodiments, the embossing height is in a range of between 0.03 inch and 0.07 inch. In some embodiments, the embossing height is about 0.01 inch. In some embodiments, the embossing height is about 0.015 inch. In some embodiments, the embossing height is about 0.02 inch. In some embodiments, the embossing height is about 0.03 inch. In some embodiments, the embossing height is about 0.04 inch. In some embodiments, the embossing height is about 0.05 inch. In some embodiments, the embossing height is about 0.06 inch. In some embodiments, the embossing height is about 0.07 inch. In some embodiments, the embossing height is about 0.08 inch.

In some embodiments, at least one indicator 100 within a set of indicators includes a haptic signature 120 that is debossed on (i.e., depressed from) the corresponding one of the surfaces 112, 114 of the indicator body 102. In some embodiments, such a haptic signature 120 is debossed to a depth that is selected so as to enable a user to identify indicia in the haptic signature 120, and thereby to identify the medicament or other substance that is contained within the tubing T to which the indicator 100 is attached. In some embodiments, the debossing depth is in a range of between 0.02 inch and 0.08 inch. In some embodiments, the debossing depth is in a range of between 0.02 inch and 0.04 inch. In some embodiments, the debossing depth is in a range of between 0.04 inch and 0.06 inch. In some embodiments, the debossing depth is in a range of between 0.06 inch and 0.08 inch. In some embodiments, the debossing depth is in a range of between 0.02 inch and 0.06 inch. In some embodiments, the debossing depth is in a range of between 0.04 inch and 0.08 inch.

In some embodiments, at least one indicator 100 within a set of indicators includes a haptic signature 120 that includes a grainy texture formed on (i.e., raised from) the corresponding one of the surfaces 112, 114 of the indicator body 102. In some embodiments, such a haptic signature 120 includes a grainy texture that is selected so as to enable a user to identify indicia in the haptic signature 120, and thereby to identify the medicament or other substance that is contained within the tubing T to which the indicator 100 is attached. In some embodiments, the grainy texture includes individual grains of varying sizes. In some embodiments, the grainy texture has a texture comparable to that of 100 grit sandpaper. In some embodiments, the grainy texture includes grains having sizes that are in a range of between 0.005 inch and 0.010 inch. In some embodiments, the grainy texture includes grains having sizes that are in a range of between 0.005 inch and 0.006 inch. In some embodiments, the grainy texture includes grains having sizes that are in a range of between 0.006 inch and 0.007 inch. In some embodiments, the grainy texture includes grains having sizes that are in a range of between 0.007 inch and 0.008 inch. In some embodiments, the grainy texture includes grains having sizes that are in a range of between 0.008 inch and 0.009 inch. In some embodiments, the grainy texture includes grains having sizes that are in a range of between 0.009 inch and 0.010 inch. In some embodiments, the grainy texture includes grains having sizes that are in a range of between 0.005 inch and 0.007 inch. In some embodiments, the grainy texture includes grains having sizes that are in a range of between 0.006 inch and 0.008 inch. In some embodiments, the grainy texture includes grains having sizes that are in a range of between 0.007 inch and 0.009 inch. In some embodiments, the grainy texture includes grains having sizes that are in a range of between 0.008 inch and 0.010 inch. In some embodiments, the grainy texture includes grains having sizes that are in a range of between 0.005 inch and 0.008 inch. In some embodiments, the grainy texture includes grains having sizes that are in a range of between 0.006 inch and 0.009 inch. In some embodiments, the grainy texture includes grains having sizes that are in a range of between 0.007 inch and 0.010 inch. In some embodiments, the grainy texture includes grains having sizes that are in a range of between 0.005 inch and 0.009 inch. In some embodiments, the grainy texture includes grains having sizes that are in a range of between 0.006 inch and 0.010 inch.

In some embodiments, at least one indicator 100 within a set of indicators includes a haptic signature 120 that includes a plurality of similar individual indicia elements (e.g., lines, curves, letters, symbols, etc.) that are spaced apart from one another along the corresponding one of the surfaces 112, 114 of the indicator body 102. In some embodiments, each such indicia element is embossed from the corresponding one of the surfaces 112, 114 to a height such as one of the embossing heights discussed above. In some embodiments, each such indicia element is debossed from the corresponding one of the surfaces 112, 114 to a depth such as one of the debossing depths discussed above. In some embodiments, such a haptic signature 120 includes indicia elements that are spaced apart from one another by a spacing distance that is selected so as to enable a user to identify the indicia elements in the haptic signature 120 as similar indicia elements that are spaced apart from one another, and thereby to identify the medicament or other substance that is contained within the tubing T to which the indicator 100 is attached. In some embodiments, the spacing distance is in a range of between 0.02 inch and 0.08 inch. In some embodiments, the spacing distance is in a range of between 0.02 inch and 0.04 inch. In some embodiments, the spacing distance is in a range of between 0.04 inch and 0.06 inch. In some embodiments, the spacing distance is in a range of between 0.06 inch and 0.08 inch. In some embodiments, the spacing distance is in a range of between 0.02 inch and 0.06 inch. In some embodiments, the spacing distance is in a range of between 0.04 inch and 0.08 inch. In some embodiments, the spacing distance is in a range of between 0.06 inch and 0.12 inch. In some embodiments, the spacing distance is in a range of between 0.06 inch and 0.08 inch. In some embodiments, the spacing distance is in a range of between 0.08 inch and 0.10 inch. In some embodiments, the spacing distance is in a range of between 0.10 inch and 0.12 inch. In some embodiments, the spacing distance is in a range of between 0.06 inch and 0.10 inch. In some embodiments, the spacing distance is in a range of between 0.08 inch and 0.12 inch.

In some embodiments, at least one indicator 100 within a set of indicators includes a haptic signature 120 that includes a series of similar individual indicia elements (e.g., lines, curves, letters, symbols, etc.) that are spaced apart from one another along the corresponding one of the surfaces 112, 114 of the indicator body 102 and are embossed from the corresponding one of the surfaces 112, 114 to an embossing height that varies among the indicia elements (e.g., each of the indicia elements has a height that is different from the heights of some or all of the remaining ones within the series of the indicia elements). In some embodiments, the varying embossing heights within such a series of indicia elements are selected so as to enable a user to recognize such indicia elements as indicia elements that are similar to one another but of varying size. In some embodiments, the indicia elements in the series have varying heights that are in a range of between 0.005 inch and 0.08 inch.

In some embodiments, at least one indicator 100 within a set of indicators includes a haptic signature 120 that includes an indicia element having a width that varies across a length thereof so as to define an expanding profile. In some embodiments, the indicia element has a width that varies across a range of between 0.05 inch and 0.5 inch. In some embodiments, the indicia element has a width that varies across a range of between 0.05 inch and 0.2 inch. In some embodiments, the indicia element has a width that varies across a range of between 0.2 inch and 0.35 inch. In some embodiments, the indicia element has a width that varies across a range of between 0.35 inch and 0.5 inch. In some embodiments, the indicia element has a width that varies across a range of between 0.05 inch and 0.35 inch. In some embodiments, the indicia element has a width that varies across a range of between 0.2 inch and 0.5 inch.

In some embodiments, at least one indicator 100 within a set of indicators includes a haptic signature 120 that includes an embossed portion and a debossed portion. In some embodiments, at least one indicator 100 within a set of indicators includes a haptic signature 120 that includes an embossed portion having an embossing height that is in one of the ranges noted above and a debossed portion. In some embodiments, at least one indicator 100 within a set of indicators includes a haptic signature 120 that includes an embossed portion and a debossed portion having a debossing depth that is one of the ranges noted above.

In some embodiments, at least one indicator 100 within a set of indicators includes a haptic signature 120 that includes an embossed portion and a debossed/indented portion within the embossed portion. In some embodiments, at least one indicator 100 within a set of indicators includes a haptic signature 120 that includes an embossed portion having an embossing height that is in one of the ranges noted above and a debossed/indented portion within the embossed portion. In some embodiments, at least one indicator 100 within a set of indicators includes a haptic signature 120 that includes an embossed portion having an embossing height that is in one of the ranges noted above and a debossed/indented portion within the embossed portion having a debossing depth that is one of the ranges noted above.

While not intended to be limiting, several examples of haptic signatures are listed in Table 1 below, along with information regarding their specific applications, metaphors, haptic and visual signatures.

TABLE 1

Haptic signatures

Figure 24A:
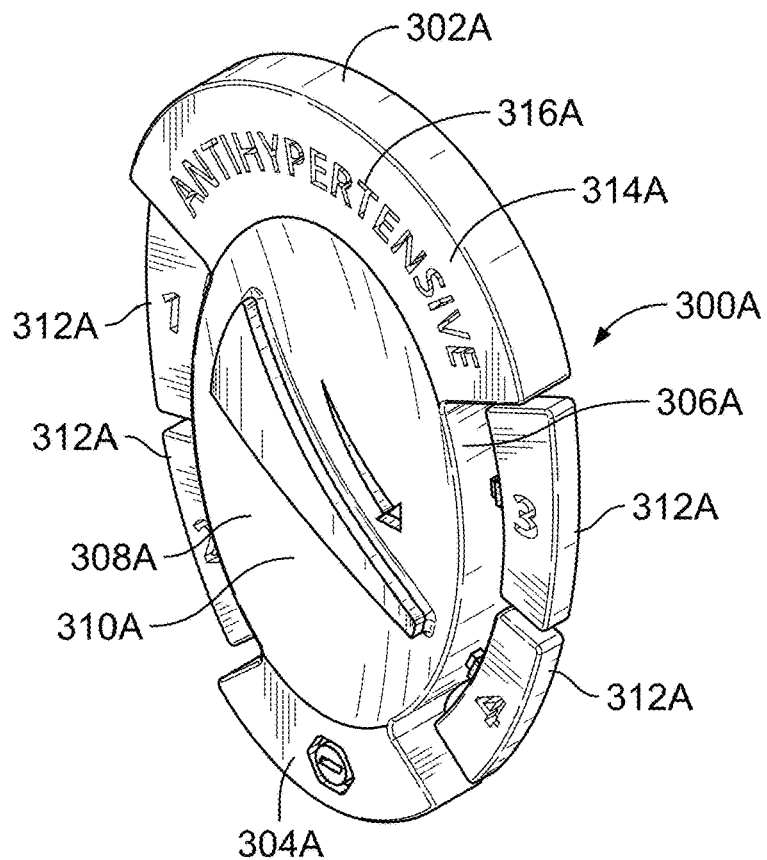
FIG. 24A is a front perspective view of another embodiment of an intravenous tubing indicator including an exemplary haptic signature/visual for an antihypertensive.
Figure 25A:
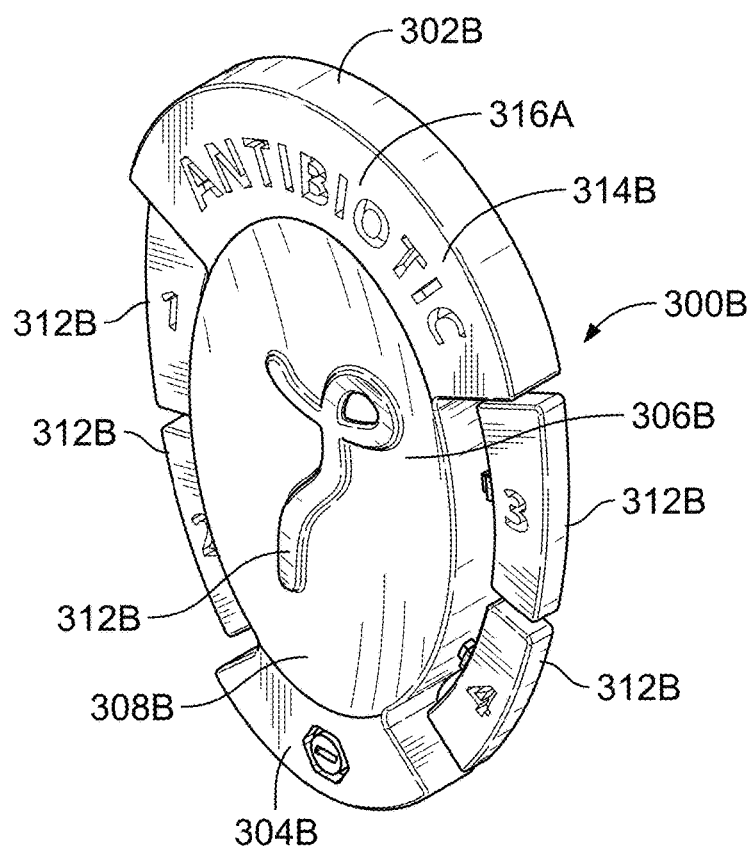
FIG. 25A is a front perspective view of another embodiment of an intravenous tubing indicator including an exemplary haptic signature/visual for an antibiotic.
Figure 26A:
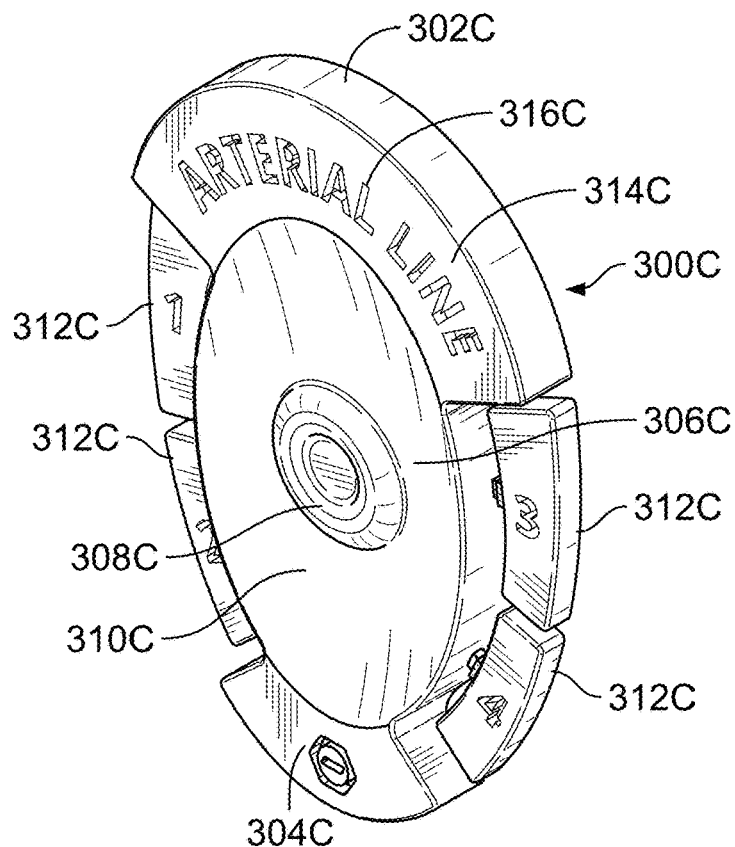
FIG. 26A is a front perspective view of another embodiment of a tubing indicator including an exemplary haptic signature/visual for an arterial line.
Figure 27A:
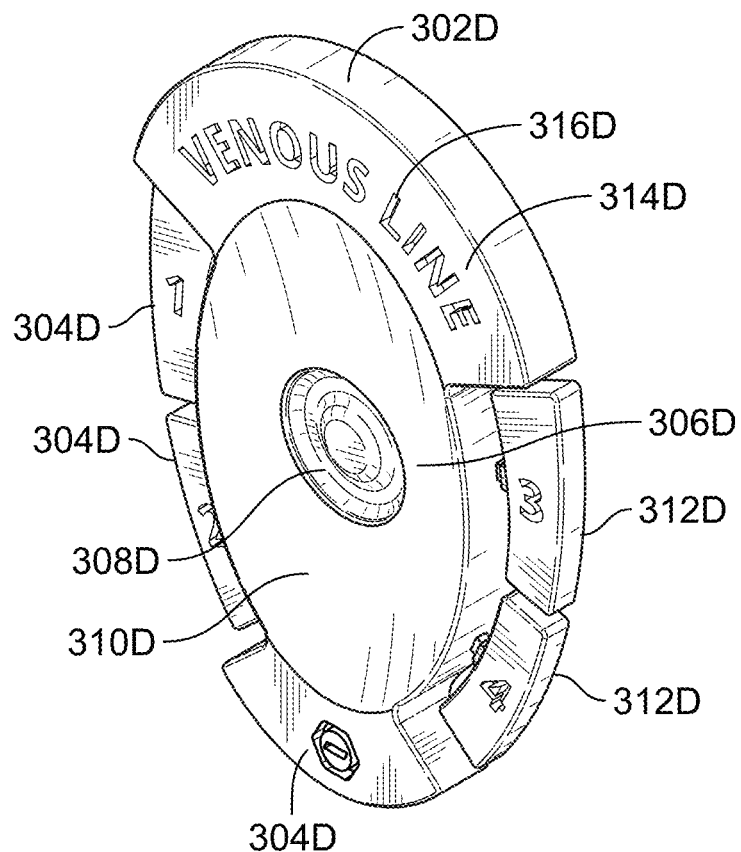
FIG. 27A is a front perspective view of another embodiment of an intravenous tubing indicator including an exemplary haptic signature/visual for a venous line.
Figure 28A:
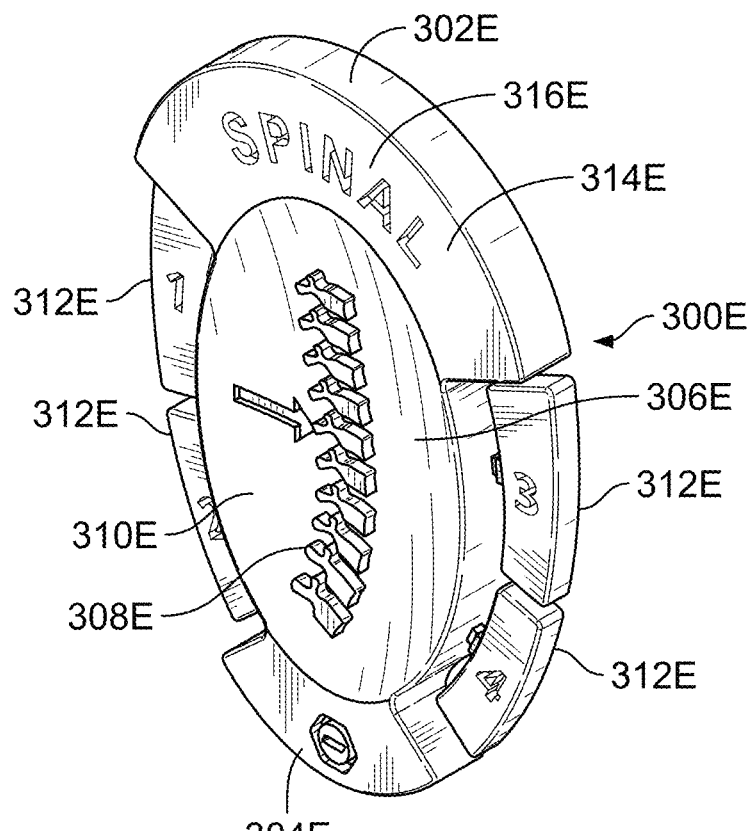
FIG. 28A is a front perspective view of another embodiment of a tubing indicator including an exemplary haptic signature/visual for spinal administration.

| Medication Type and/or Haptic Category | Metaphor | Haptic | Signature/Visual and Corresponding Representative Figure |
|---|---|---|---|
| GoTo | Maintenance line; open line; safe line; including a directional arrow; push line | Raised "GoTo" logo/lettering. | Lettering as shown in FIGS. 6 and 15 |
| Antihypertensive | Control blood pressure | Wide higher raised surface that gradually changes to a thin/low raised surface. Opposite direction of "Pressors." Downward angle from top left to bottom right. High and wide surface represents higher blood pressure and the thin/low surface represents a controlled blood pressure. User traces wide surface that gradually gets thinner for the finger to follow. | Wide surface lowering to a thin surface resembling graph or on ramp as shown in FIG. 24A |
| Antibiotics | Germs/bacteria | Bacteria or germ in a worm shape. Organic shape and path with a loop indicating movement. | Bacteria like shape that is in the shape of a squiggle line that is overlapping itself. User feels a thin smooth curved line that overlaps, as shown in FIG. 25A |
| Arterial Line | Blood cell; bright red; oxygen rich blood | Red blood cell. Raised circular red blood cell with indentation in the middle as a metaphor for oxygen rich blood. User feels embossed smooth circular shape with indentation. | Embossed red blood cell (red tag) as shown in FIG. 26A |
| Venous Line | Blood cell; blue; oxygen poor blood | Red blood cell. Debossed red blood cell as a metaphor for oxygen poor blood. Reverse of arterial line. User feels debossed smooth circular shape. | Debossed red blood cell (blue tag) as shown in FIG. 27A |
| Spinal Applications | Spinal cord | Lateral view of spine. Enough spacing between the bodies of vertebrae and spinous process' for the fingers to distinguish different vertebrae. User feels column of raised surfaces evenly spaced with protruding rounded sections out of each surface. | Lateral view of spine as shown in FIG. 28A |

TABLE 1-continued

Haptic signatures

Figure 29:
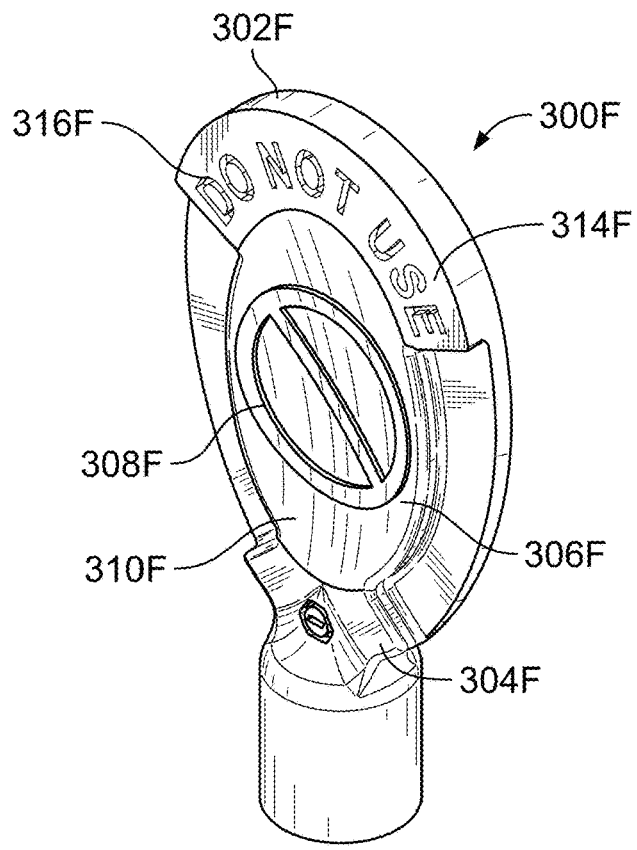
FIG. 29 is a front perspective view of another embodiment of a tubing indicator including an exemplary haptic signature/visual for a port cover (Do Not Use)
Figure 30:
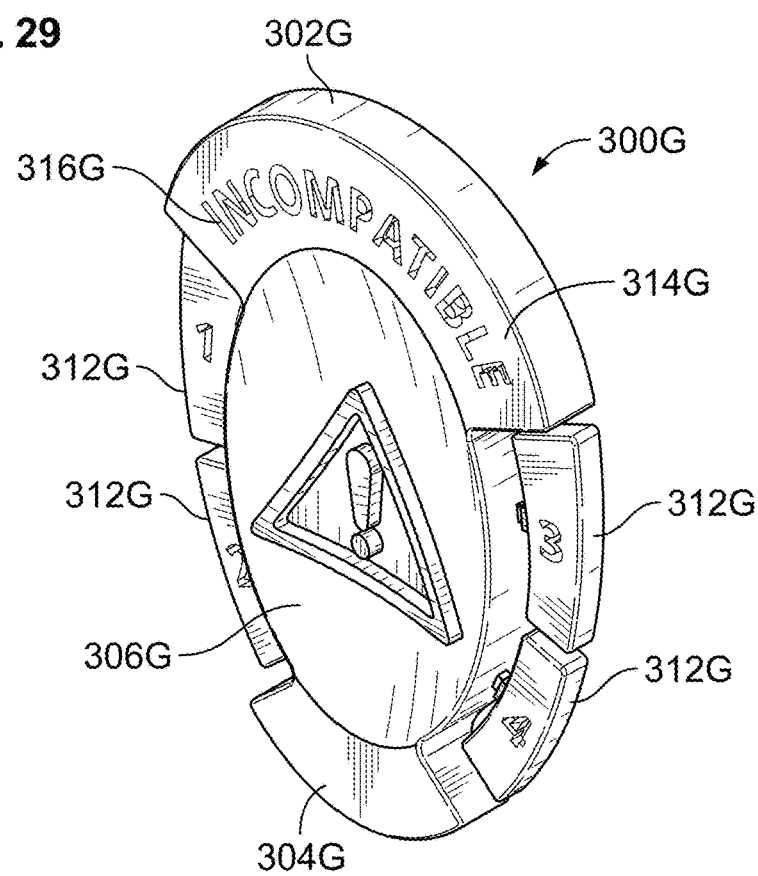
FIG. 30 is a front perspective view of another embodiment of a tubing indicator including an exemplary haptic signature/visual for incompatible medications (i.e., to be administered alone)
Figure 31:
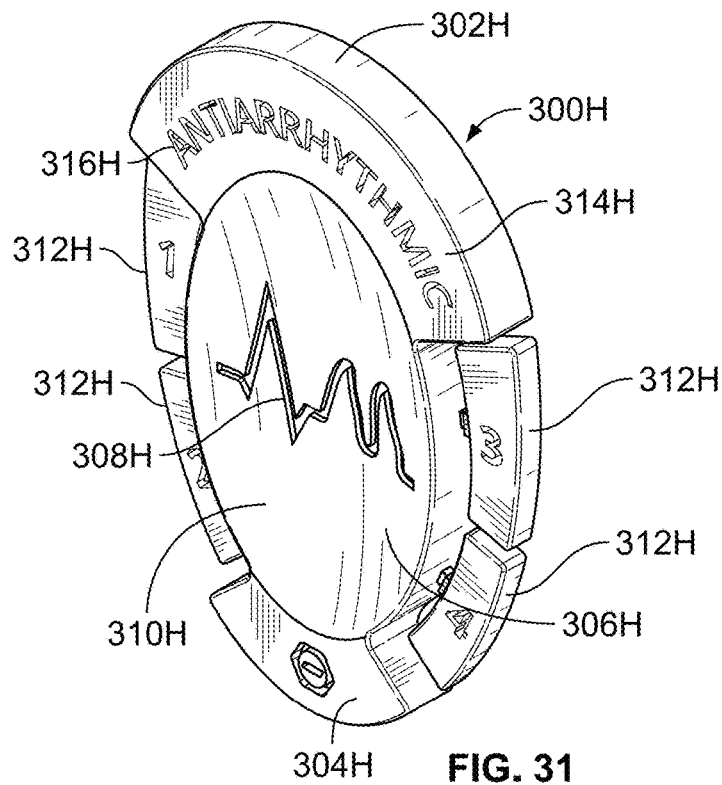
FIG. 31 is a front perspective view of another embodiment of an intravenous tubing indicator including an exemplary haptic signature/visual for an antiarrhythmic.
Figure 32:
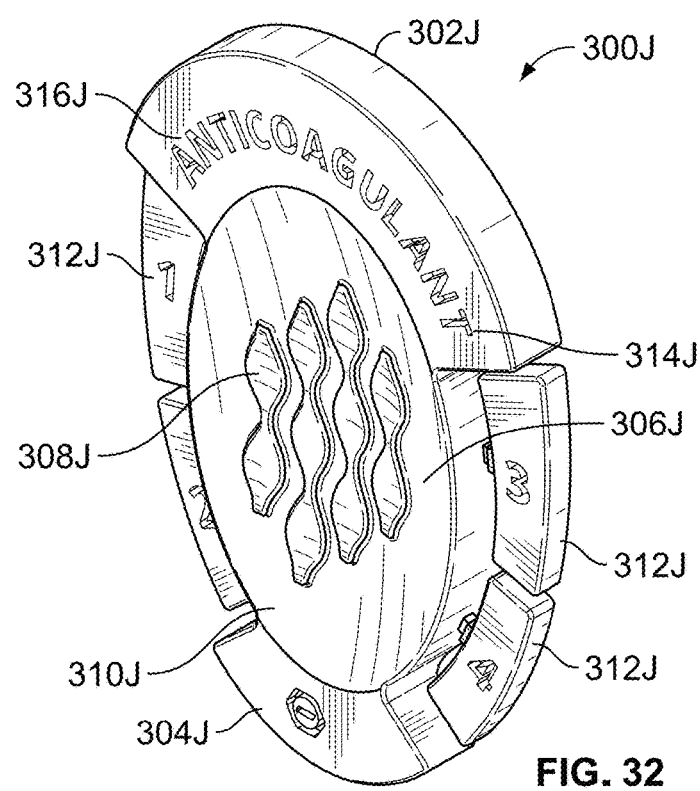
FIG. 32 is a front perspective view of another embodiment of an intravenous tubing indicator including an exemplary haptic signature/visual for an anticoagulant.
Figure 33:
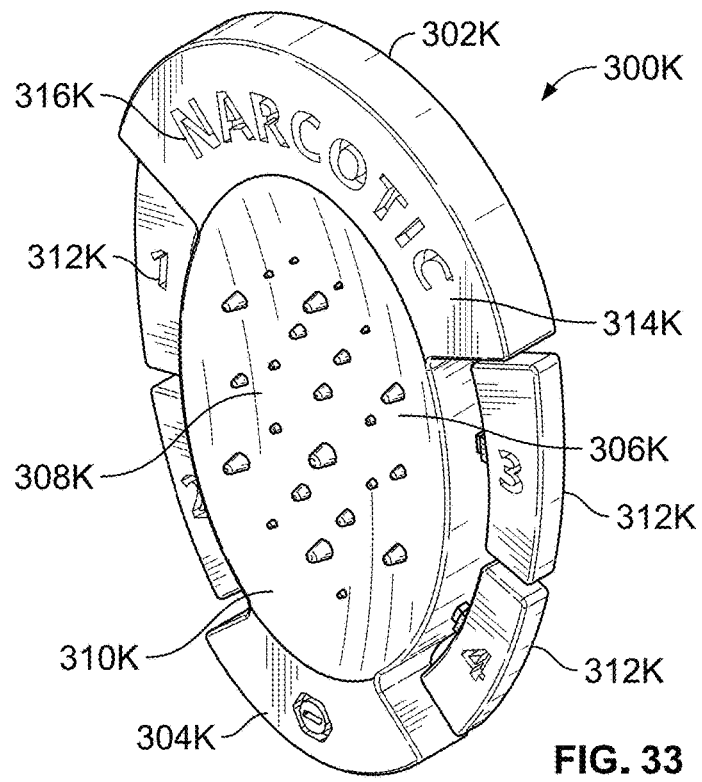
FIG. 33 is a front perspective view of another embodiment of an intravenous tubing indicator including an exemplary haptic signature/visual for a narcotic.
Figure 34:
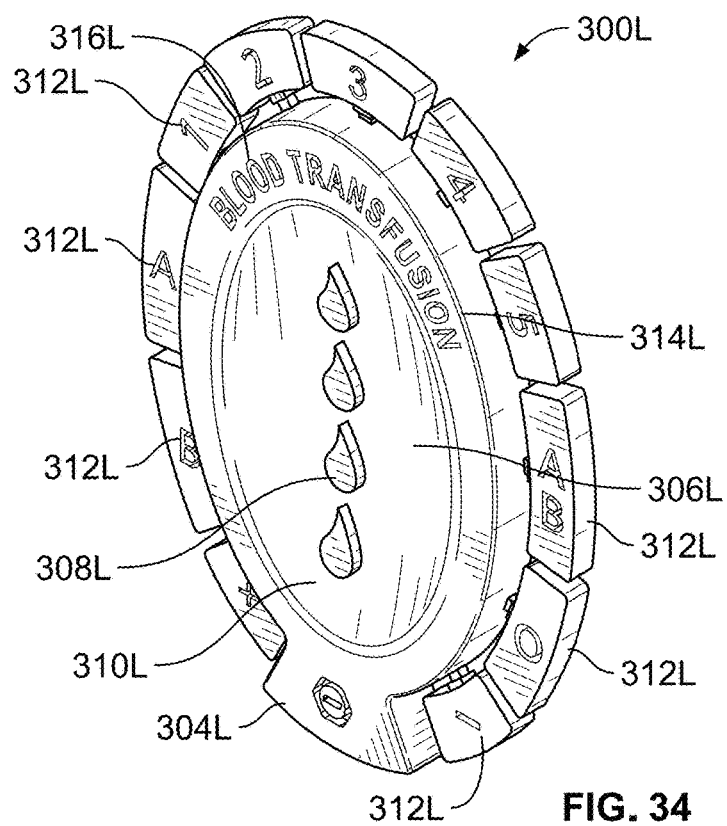
FIG. 34 is a front perspective view of another embodiment of an intravenous tubing indicator including an exemplary haptic signature/visual for blood transfusion.

| Medication Type and/or Haptic Category | Metaphor | Haptic | Signature/Visual and Corresponding Representative Figure |
|---|---|---|---|
| Line port cover | Incompatible Tag that blocks entry to port | Port cover, DO NOT USE | "Do Not Use" cover as shown in FIG. 29 |
| Incompatible | Must be given alone | Triangle with exclamation point indicating to users do not mix/enter/combine. Raised even surface. | Triangle with exclamation point as shown in FIG. 30 |
| Antiarrhythmics | Wavy, flowy, (EKG wave) (e.g., common irregular heart rhythm) | Normal heartbeat that changes into an arrhythmia. Thin debossed wave creates the waves of the EKG. This texture is set to be on a flat surface so that the only texture available for the finger to identify is the EKG waves. Half of the texture is made to show normal heart rhythm with sharp points/paths and the second half being an irregular long, wavy, and rounded path. User feels sharp and clean edge/line transitioning to rounded sporadic edge/line | Normal EKG waves transitioning to irregular EKG wave as shown in FIG. 31 |
| Anticoagulant | Wave and flow | Waving debossed lines to indicate standard blood flow. Lines should have enough separation to distinguish between lines. User feels series of lines flowing and waving back and forth running vertically. | Waves of flowing lines as shown in FIG. 32 |
| Narcotics | Prickly, agitated, loopy/spacey | Prickly texture with inconsistent heights and spacing as a metaphor for being loopy/spacey and confused. Varying heights of texture. User feels inconsistent prickly texture pressing into finger at different heights, spacing, and sizes. | Sporadic spikey texture as shown in FIG. 33 |
| Blood Transfusion | blood, blood drop | Blood drop or multiple drops of blood. Raised smooth surface that starts at a point and rounds out at the bottom. | Blood drop symbol(s) as shown in FIG. 34 |
| Pressors | Squeeze/causing a rise in blood pressure. | Thin lower raised surface that | Thin surface rising to wider surface resembling graph or |

TABLE 1-continued

Haptic signatures

Figure 35:
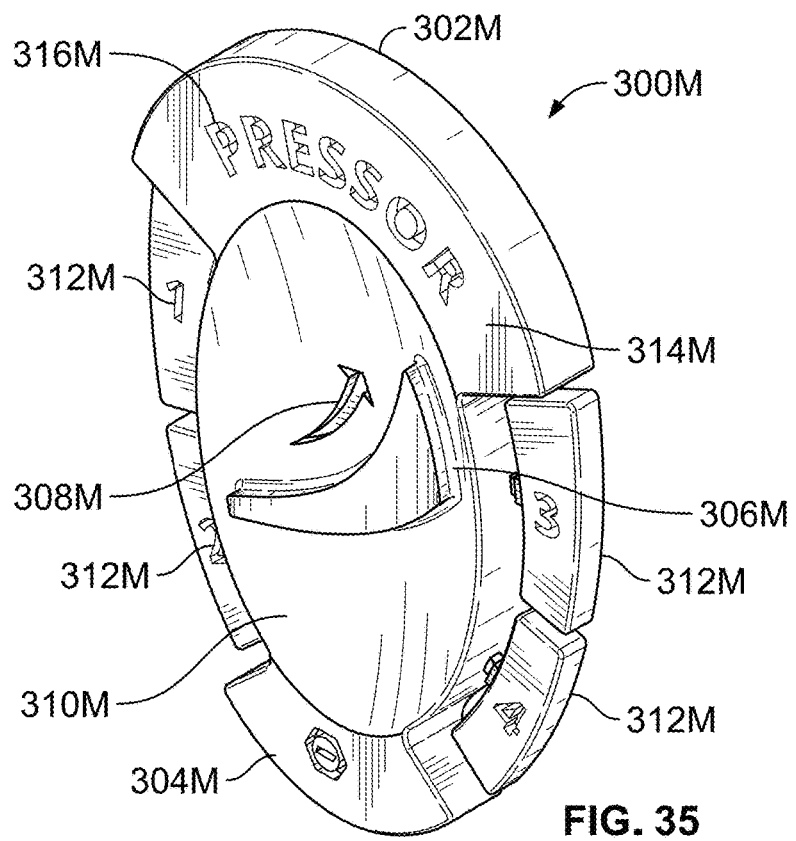
FIG. 35 is a front perspective view of another embodiment of an intravenous tubing indicator including an exemplary haptic signature/visual for a pressor.
Figure 36:
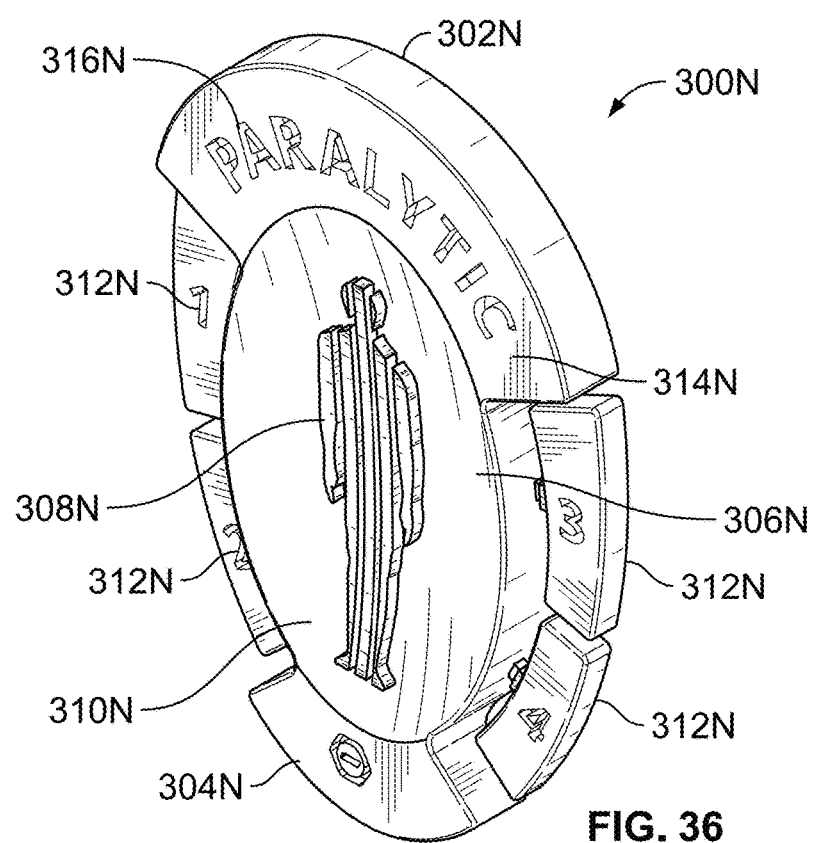
FIG. 36 is a front perspective view of another embodiment of an intravenous tubing indicator including an exemplary haptic signature/visual for a paralytic.
Figure 37:
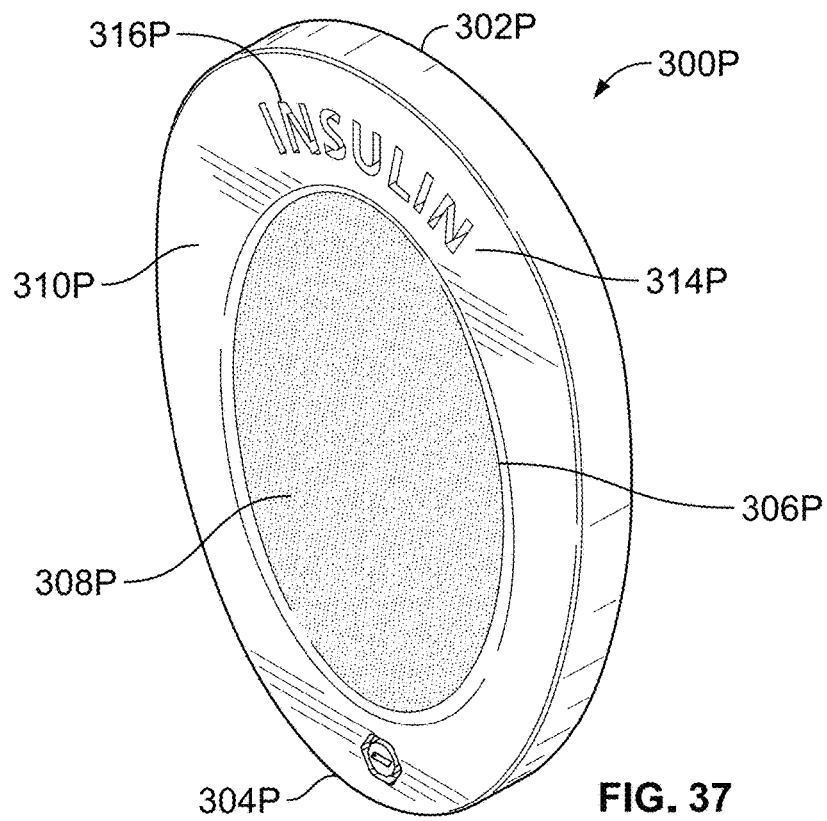
FIG. 37 is a front perspective view of another embodiment of an intravenous tubing indicator including an exemplary haptic signature/visual for insulin.
Figure 38:
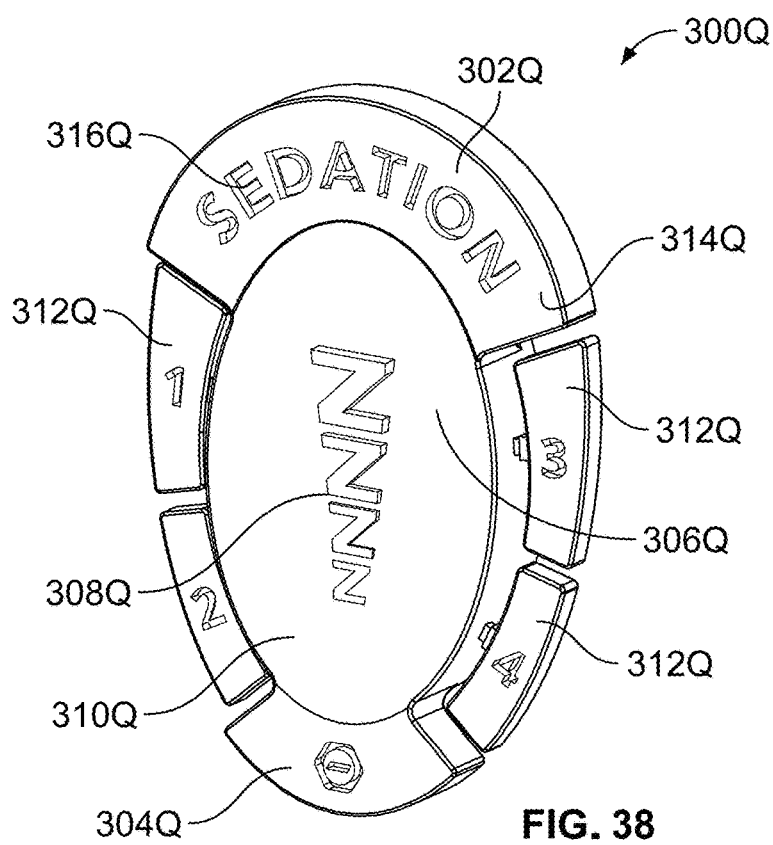
FIG. 38 is a front perspective view of another embodiment of an intravenous tubing indicator including an exemplary haptic signature/visual for a sedative (i.e., sedation)
Figure 39:
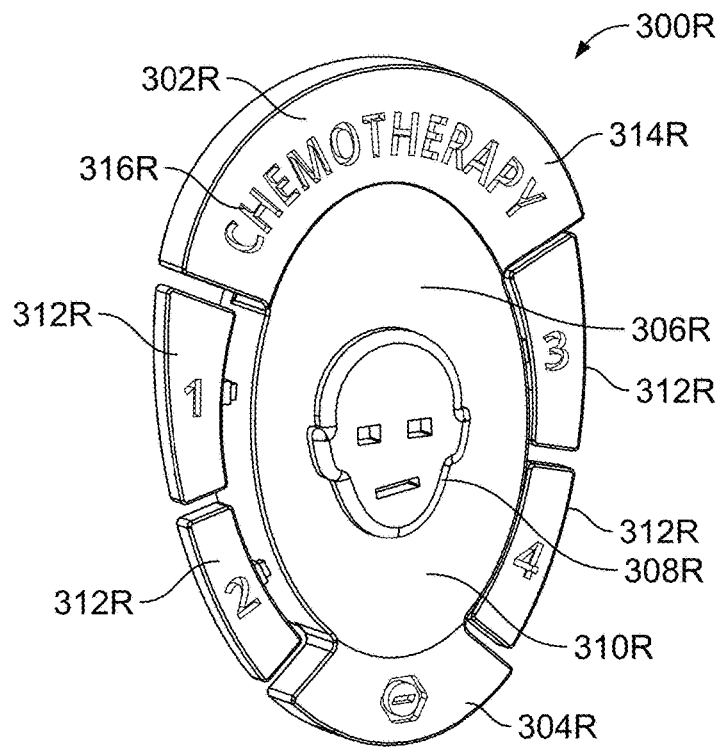
FIG. 39 is a front perspective view of another embodiment of an intravenous tubing indicator including an exemplary haptic signature/visual for chemotherapy.

| Medication Type and/or Haptic Category | Metaphor | Haptic | Signature/Visual and Corresponding Representative Figure |
|---|---|---|---|
| | | gradually changes into a wide higher raised surface from bottom left to top right. Thin and low represents low blood pressure and the upwards increase in size and height represents high blood pressure. User traces thin surface that gradually gets wider for the finger to follow. | offramp as shown in FIG. 35 |
| Paralytics | Rigidity; rigid | Raised human figure with rigid lines running through body. The form of the figure is made up of rigid vertical lines at different lengths to create the shape of the body. Spacing in between vertical lines show that the body is rigid throughout with no organic, wavy, or soft lines present. Rigid lines should have enough spacing between them to distinguish individual lines. User feels different length vertical lines that create a figure. | Human form with straight lines running from head to toe as shown in FIG. 36 |
| Insulin | Course, sandpaper-like and granular | Sandpaper style texture made of small grains to mimic the feel of sugar. | Small rough and grainy texture as shown in FIG. 37 |
| Sedation/ Sedative | Letter Z; sleepy; calm | Gradually descending "Z's." Multiple letter Z's in a vertical alignment. Z's at the top are larger and raised surfaces that gradually descend in size and in raised height until the Z is no longer a raised surface. User feels raised texture that gradually goes to smooth flat surface blending into the background of the haptic tag. | Large Z's gradually getting smaller as shown in FIG. 38 |
| Chemotherapy | Hairy/fuzzy, bald, pale color/lime green (nausea) | Smooth and bald head/face. Front facing head with a slight frown or unsettled expression. Raised smooth/round surface with no | Unsettled bald face as shown in FIG. 39 |

TABLE 1-continued

Haptic signatures

Figure 40:
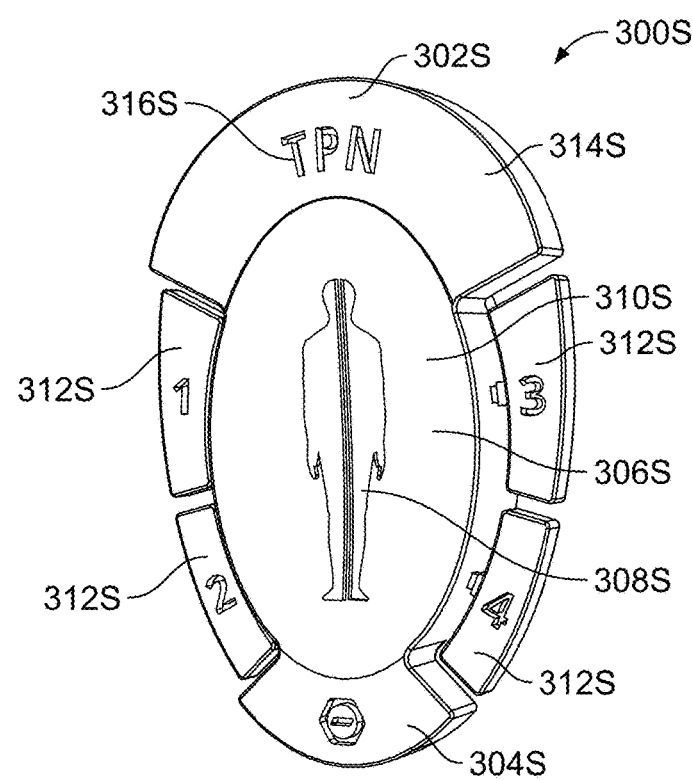
FIG. 40 is a front perspective view of another embodiment of an intravenous tubing indicator including an exemplary haptic signature/visual for total parenteral nutrition (TPN)
Figure 41:
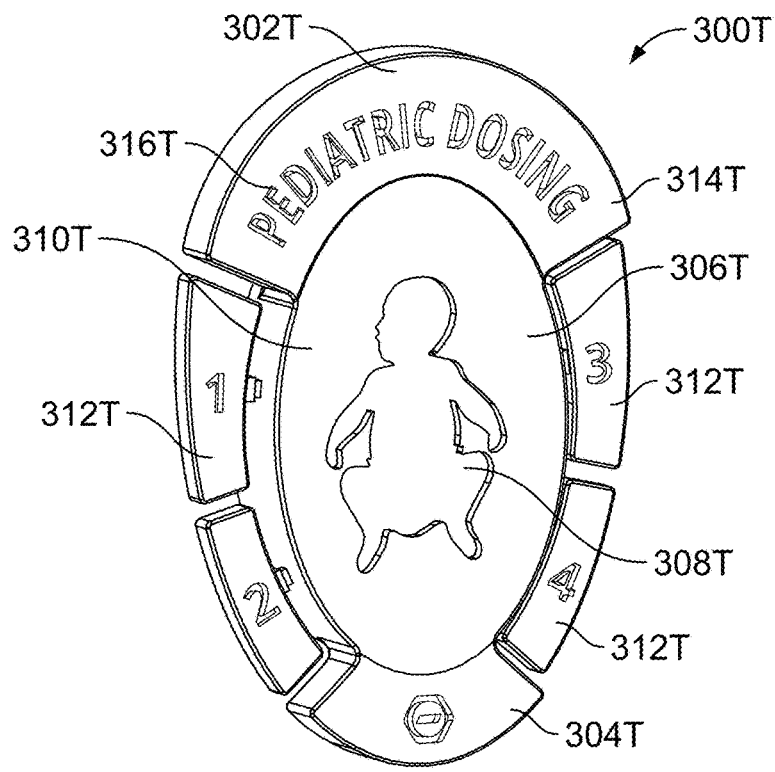
FIG. 41 is a front perspective view of another embodiment of an intravenous tubing indicator including an exemplary haptic signature/visual for pediatric dosing.
Figure 42:
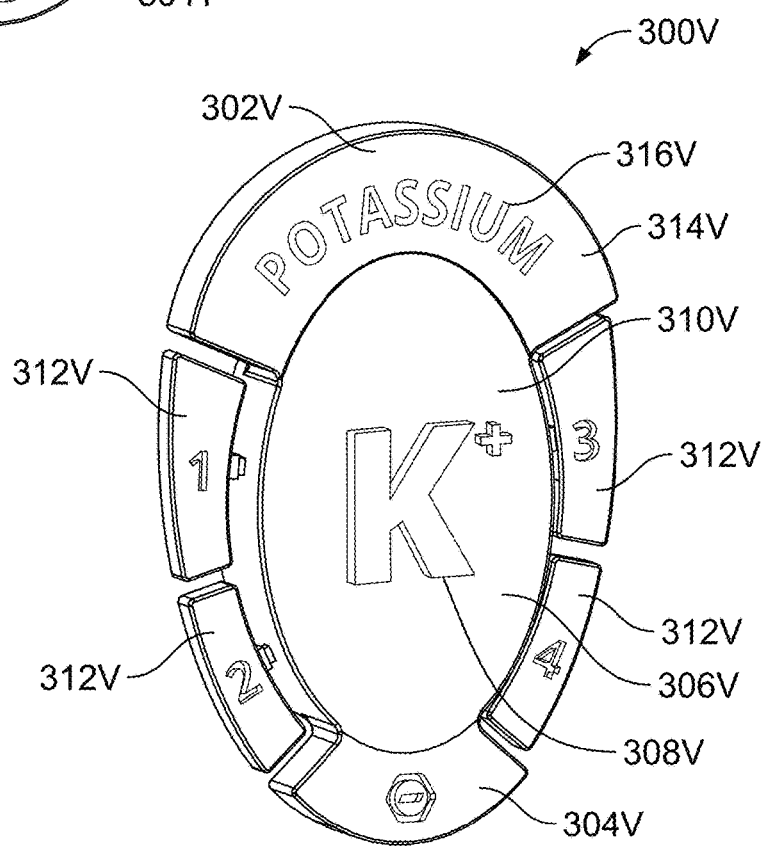
FIG. 42 is a front perspective view of another embodiment of an intravenous tubing indicator including an exemplary haptic signature/visual for potassium.
Figure 43:
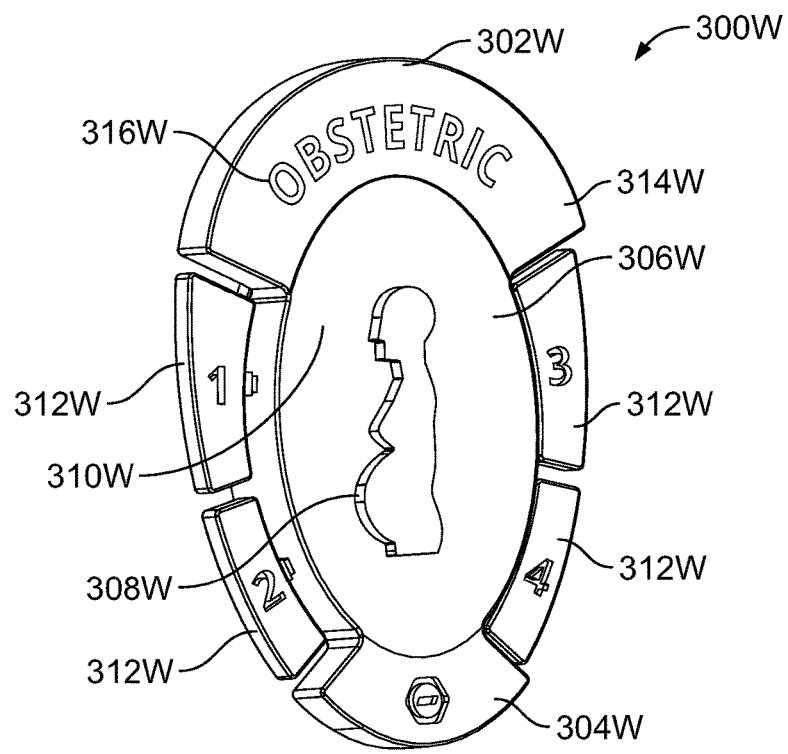
FIG. 43 is a front perspective view of another embodiment of an intravenous tubing indicator including an exemplary haptic signature/visual for obstetric administration.

| Medication Type and/or Haptic Category | Metaphor | Haptic | Signature/Visual and Corresponding Representative Figure |
|---|---|---|---|
| | | hard edges that is completely bald. User feels smooth embossed surface with facial features. | |
| TPN | Total parenteral nutrition, food/amino acids-building blocks of protein/complete substance | Half embossed human figure/half debossed human figure. Figure is split vertically and divided into two sections. The left section is embossed while the right is debossed to show full vs. empty. The left showing full of nutrients and the right showing empty with no nutrients. User feels an embossed form next to its mirrored image debossed form. | Human form that is embossed on the left and debossed on the right as shown in FIG. 40 |
| Pediatric Dosing | Baby/child | Baby figure. Raised surface of baby laying on its back. Smooth raised surface with human features (arms, head, legs) | Debossed raised surface shape of a newborn baby as shown in FIG. 41 |
| Potassium | Letter K$^+$ | Letter "K$^+$" for chemical symbol for potassium. Raised even surface. Large enough surface that users can feel/draw the "K" with their finger. User feels crisp and hard edges of embossed shape. | Embossed letter K$^+$ as shown in FIG. 42 |
| Obstetrics Application | Mother/child | Raised surface of pregnant woman's head and torso. User feels embossed smooth surface - organic form with smaller features and large smooth rounded surface | Pregnant female figure as shown in FIG. 43 |

As illustrated in Table 1, the haptic signatures may correspond to various classes of medications (e.g., narcotics, anticoagulants, antiarrhythmics and antibiotics), as well as specific types of applications or dosing (e.g., obstetrics and spinal applications, pediatric dosing), functions (e.g., "GoTo" maintenance line (which is further discussed below) and line port cover) or anatomical designations (e.g., arterial or venous lines). These haptic signatures are configured to be easily learned, and remembered, by the caregiver, patient and patient advocate.

In addition to the haptic signatures, each indicator 100 may have a specific color and/or shape that is associated with the various classes of medications, specific types of applications or dosing, functions or anatomical designations. Each indicator 100 may further include a specific luminosity (i.e., glowing in the dark) as a further identifying characteristic. The combination of the identifying characteristics of color, shape, luminosity and haptic signature imbue each indicator 100 with a unique, multi-sensory characteristic, or communication. As discussed above, the specific combinations of multi-sensory communications alert not only the user (but also the patient, family or patient advocate) to the contents of the intravenous tubing (e.g., different classes or types of medications or fluids) and enable the user to take appropriate action in connection therewith. By the patient, family, patient advocate being aware of the medication in use, this provides another level of checks and balances to minimize or prevents medication-related errors that can be catastrophic, and even fatal.

In one embodiment, each indicator 100 includes at least three of the aforesaid identifying characteristics. In another embodiment, each indicator 100 includes at least four of the aforesaid identifying characteristics. In another embodiment, each indicator 100 includes at least five of the aforesaid identifying characteristics. In addition to the identifying characteristics discussed above, text (i.e., alphanumeric indicia) also constitutes one identifying characteristic in some embodiments.

FIGS. 7-22 illustrate a second embodiment of an intravenous tubing indicator 200 according to the present disclosure. The indicator 200 includes a body 202 that is formed from two cooperating members 202a and 202b. Each of the members 202a, 202b has two opposed ends 204a, 206a and 204b, 206b, respectively. When the members 202a, 202b are secured together (see FIGS. 7-15), the respective ends 204a, 206a and 204b, 206b cooperate to form opposed ends 204, 206 of the body 202.

Referring now to FIGS. 16-22, the member 202a has opposed sides 208a, 210a that extend between ends 204a, 206a, and opposed inner and outer surfaces 211, 212 that extend between ends 204a, 206a and are bordered by sides 208a, 210a. The end 204a defines a partial aperture 216a therein and the end 206a defines a partial aperture 218a therein. The inner surface 211 defines a channel 215 that extends between partial apertures 216a, 218a, and is continuous therewith. The member 202a also includes one or more slots 217 formed therein, between the inner and outer surfaces 211, 212. In one exemplary embodiment, there are three slots 217 (see FIGS. 16 and 18). The channel 215 and slots 217 are discussed below.

With continued reference to FIGS. 16-22, the member 202b has a somewhat similar construction to that of the member 202a. The member 202b has opposed sides 208b, 210b that extend between ends 204b, 206b, and opposed inner and outer surfaces 213, 214 that extend between ends 204b, 206b and are bordered by sides 208b, 210b. When the members 202a, 202b are secured together (see FIGS. 7-15), the respective sides 208a, 210a and 208b, 210b cooperate to form opposed sides 208, 210 of the body 202. The end 204b defines a partial aperture 216b therein and the end 206b defines a partial aperture 218b therein. The inner surface 213 defines a channel 219 that extends between partial apertures 216b, 218b, and is continuous therewith. The inner surface 213 also includes one or more tabs 221 extending therefrom. In one exemplary embodiment, there are three tabs 221 (see FIGS. 16 and 18). The channel 219 and tabs 221 are discussed below.

Members 202a and 202b are connected to each other by one or more hinges 222, which extend between the side 210a and 210b. In one exemplary embodiment, there are three hinges 222 (see FIGS. 17, 18, 21 and 22). The hinges 222 enable the indicator body 202 to be moved from an open to a closed position, in which members 202a and 202b fully overlap and engage one another (see FIGS. 7-15). When the body 202 is in its closed position, partial apertures 216a, 216b cooperate to form an aperture 216 at end 204, and partial apertures 218a, 218b cooperate to form an aperture 218 at end 206. The channels 215, 219 also cooperate when the body 202 is in its closed position to form a bore (not shown). The bore and apertures 216, 218 are dimensioned to receive a length of intravenous tubing T therethrough. More particularly, and as shown in FIGS. 14 and 15, the intravenous tubing T is inserted through aperture 216, extended through the bore within the interior of the indicator body 202, and exits therefrom through aperture 118 (not shown). Members 202a and 202b are secured to each other via insertion of the tabs 221 through their respective slots 217, to maintain the body 202 in its closed position. In some embodiments, the channels 215, 219 are sized and shaped so as to clasp the intravenous tubing T and prevent the intravenous tubing indicator 200 from sliding along the intravenous tubing T.

At least one of the outer surfaces 212, 214 of members 202a, 202b includes a haptic signature 220. The haptic signature 220 is similar to that of the haptic signature 120 in the first embodiment, in that it may include images, designs, numbers, letters, punctuation marks, patterns, other indicia, or any combination thereof, and is formulated to convey the nature of the medication or other substance that is contained within the intravenous tubing T and being delivered to the patient thereby. The haptic signature 220 is formed on the outer surface(s) 212 and/or 214 by any means known in the art, as discussed in connection with the indicator 100 above. The indicator 200 may have the same or similar haptic signatures as those set out in Table 1 above.

Figure 23:
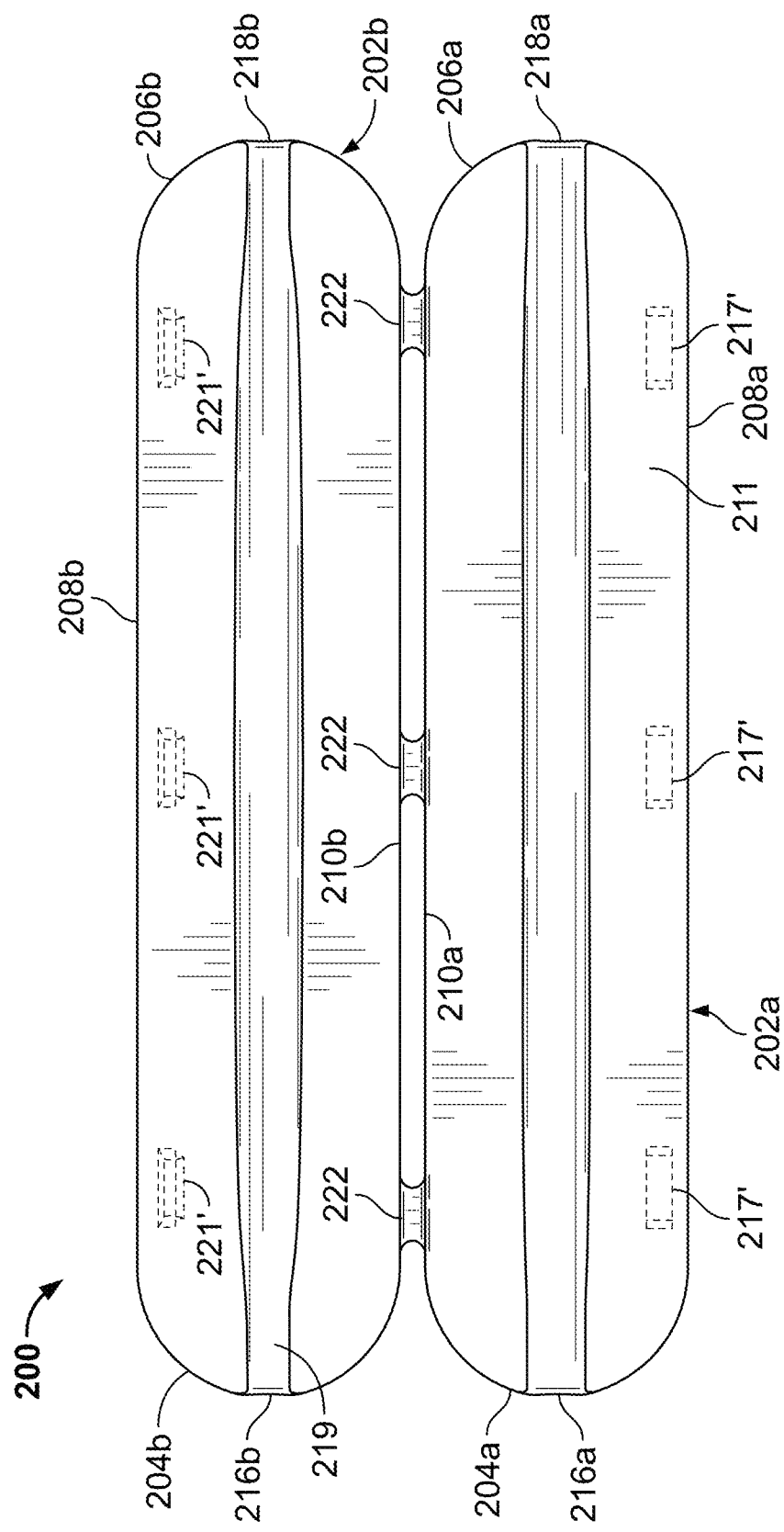
FIG. 23 is a bottom plan view of another embodiment of the intravenous tubing indicator, with interior fastening elements.

FIG. 23 illustrates another embodiment of the intravenous tubing indicator 200, wherein the interior fastening elements (i.e., slots 217' and tabs 221') can be of any suitable size and shape.

Figure 24B:
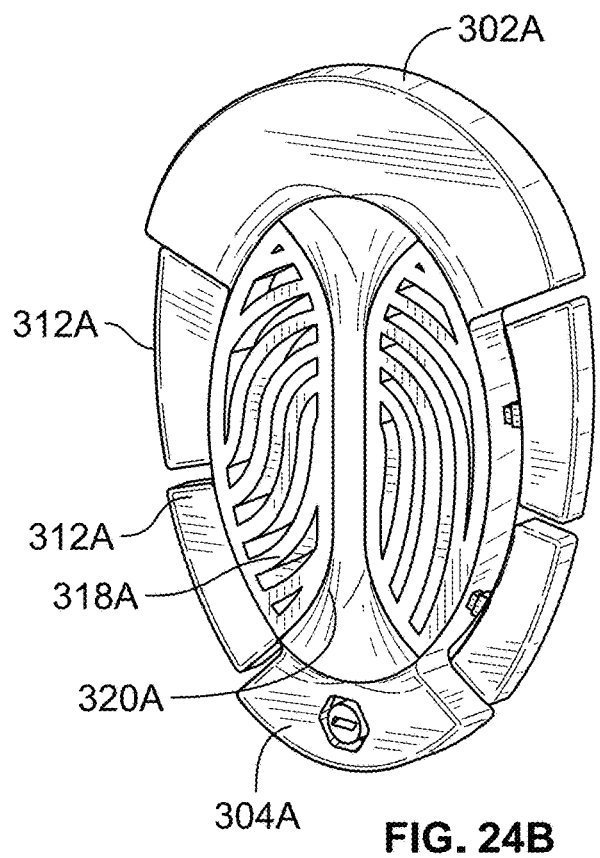
FIG. 24B is a rear perspective view of the intravenous tubing indicator of FIG. 24A.

FIGS. 24A and 24B illustrate another embodiment of the intravenous tubing indicator 300A, which includes opposed peripheral portions 302A, 304A, a central portion 306A including a haptic signature 308A for an antihypertensive on a front surface 310A thereof, and a plurality of tabs 312A extending from the central portion 306A (as discussed above) between the opposed peripheral portions 302A, 304A. The tabs 312A are numbered. In an embodiment, the tabs 312A are sequentially numbered pull or twist-off tabs to indicate the number of IV bags a patient has used during a period of time. The peripheral portion 302A includes a front surface 314A with identifying indicia 316A. FIG. 24B illustrates the rear surface 318A, in which a channel 320A is formed. The channel 320A is dimensioned to securely receive an IV line/tube therein. In some embodiments, the channel 320 is sized and shaped so as to prevent the intravenous tubing indicator 300A from sliding along an IV line/tube that has been received therein. In some embodiments, the intravenous tubing indicator 300a includes a clasp or other similar retention mechanism positioned and configured so as to facilitate retention of an IV line/tube in the channel 320A.

Figure 25B:
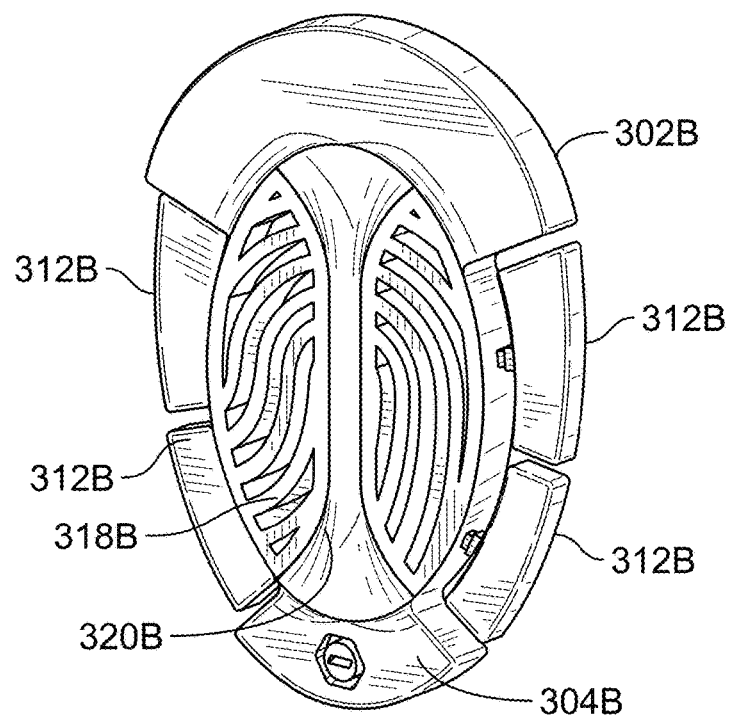
FIG. 25B is a rear perspective view of the intravenous tubing indicator of FIG. 25A.

FIGS. 25A and 25B illustrate another embodiment of the intravenous tubing indicator 300B, which includes the same structural features as the intravenous tubing indicator 300A of FIGS. 24A and 24B (designated herein with a B), except for a haptic signature 308B and identifying indicia 316B for an antibiotic.

Figure 26B:
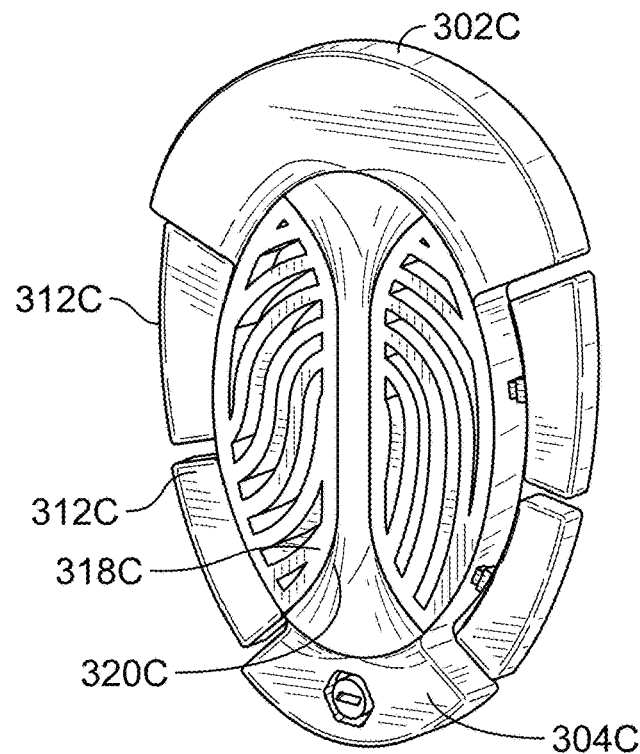
FIG. 26B is a rear perspective view of the tubing indicator of FIG. 26A.

FIGS. 26A and 26B illustrate another embodiment of the vascular tubing indicator 300C, which includes the same structural features as the intravenous tubing indicator 300A of FIGS. 24A and 24B (designated herein with a C), except for a haptic signature 308C and identifying indicia 316C for an arterial line.

Figure 27B:
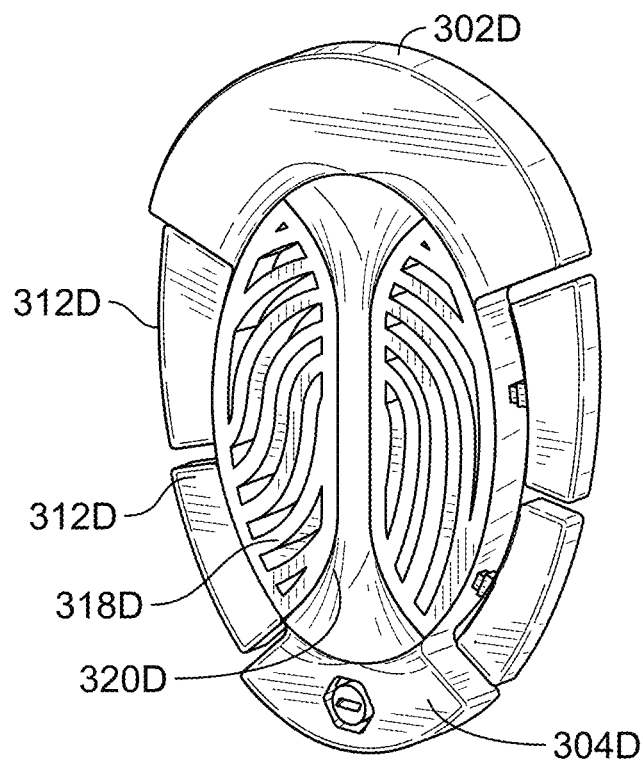
FIG. 27B is a rear perspective view of the intravenous tubing indicator of FIG. 27A.

FIGS. 27A and 27B illustrate another embodiment of the tubing indicator 300D, which includes the same structural features as the intravenous tubing indicator 300A of FIGS.

24A and 24B (designated herein with a D), except for a haptic signature 308D and identifying indicia 316D for a venous line.

Figure 28B:
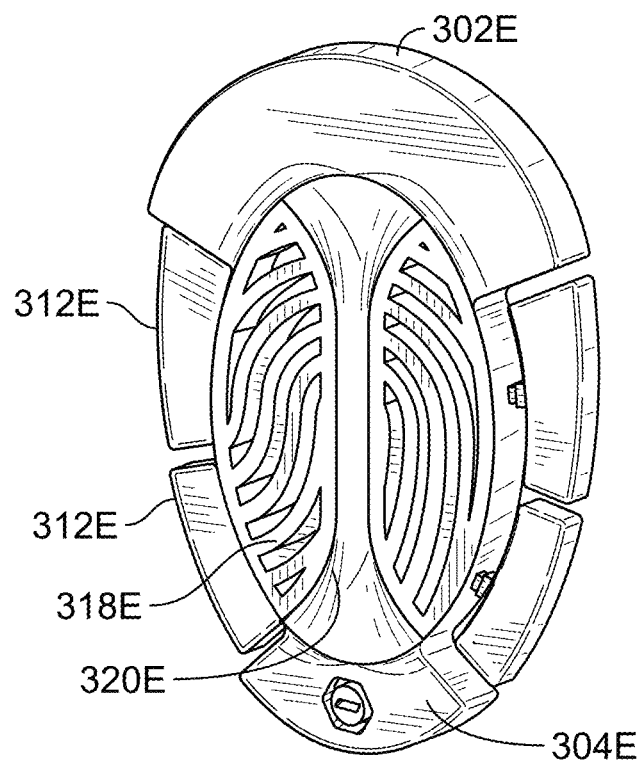
FIG. 28B is a rear perspective view of the tubing indicator of FIG. 28A.

FIGS. 28A and 28B illustrate another embodiment of the intravenous tubing indicator 300E, which includes the same structural features as the intravenous tubing indicator 300A of FIGS. 24A and 24B (designated herein with an E), except for a haptic signature 308E and identifying indicia 316E for spinal administration (which may also be referred to as "intrathecal administration").

FIGS. 29-43 illustrate further embodiments of the intravenous tubing indicator, as discussed below. While not illustrated herein, it is to be understood that the rear surfaces of such embodiments are generally the same as those shown in FIGS. 24B, 25B, 26B, 27B and 28B, including a channel that is dimensioned to securely receive an IV line/tube therein.

FIG. 29 illustrates another embodiment of the tubing indicator 300F (e.g., for arterial, venous, or spinal lines), which includes most of the same structural features as the intravenous tubing indicator 300A of FIGS. 24A and 24B (designated herein with an F), except for a port cover haptic signature 308F and Do Not Use identifying indicia 316F. In an embodiment, the tubing indicator 300F also lacks tabs. In some embodiments, the intravenous tubing indicator 300F includes an attachment portion that is sized and shaped to attach to and cover a port that is used to administer medication into an intravenous, arterial, or spinal line, thereby preventing medication from being administered into the intravenous, arterial, or spinal line.

FIG. 30 illustrates another embodiment of the intravenous tubing indicator 300G, which includes most of the same structural features as the tubing indicator 300A of FIGS. 24A and 24B (designated herein with a G), except for an incompatible haptic signature 308G and identifying indicia 316G.

FIG. 31 illustrates another embodiment of the intravenous tubing indicator 300H, which includes most of the same structural features as the intravenous tubing indicator 300A of FIGS. 24A and 24B (designated herein with a H), except for an antiarrhythmic haptic signature 308H and identifying indicia 316H.

FIG. 32 illustrates another embodiment of the intravenous tubing indicator 300J, which includes most of the same structural features as the intravenous tubing indicator 300A of FIGS. 24A and 24B (designated herein with a G), except for an anticoagulant haptic signature 308J and identifying indicia 316J.

FIG. 33 illustrates another embodiment of the intravenous tubing indicator 300K, which includes most of the same structural features as the intravenous tubing indicator 300A of FIGS. 24A and 24B (designated herein with a K), except for a narcotic haptic signature 308K and identifying indicia 316K.

FIG. 34 illustrates another embodiment of the intravenous tubing indicator 300L, which includes most of the same structural features as the intravenous tubing indicator 300A of FIGS. 24A and 24B (designated herein with an L), except for a blood transfusion haptic signature 308L and identifying indicia 316L. The intravenous tubing indicator 300L also includes more tabs than other embodiments.

FIG. 35 illustrates another embodiment of the intravenous tubing indicator 300M, which includes most of the same structural features as the intravenous tubing indicator 300A of FIGS. 24A and 24B (designated herein with an M), except for a pressor haptic signature 308M and identifying indicia 316M.

FIG. 36 illustrates another embodiment of the intravenous tubing indicator 300N, which includes most of the same structural features as the intravenous tubing indicator 300A of FIGS. 24A and 24B (designated herein with an N), except for a paralytic haptic signature 308N and identifying indicia 316N.

FIG. 37 illustrates another embodiment of the intravenous tubing indicator 300P, which includes most of the same structural features as the intravenous tubing indicator 300A of FIGS. 24A and 24B (designated herein with a P), except for an insulin haptic signature 308P and identifying indicia 316P. The intravenous tubing indicator 300P also lacks tabs, as discussed above.

FIG. 38 illustrates another embodiment of the intravenous tubing indicator 300Q, which includes most of the same structural features as the intravenous tubing indicator 300A of FIGS. 24A and 24B (designated herein with a Q), except for a sedative haptic signature 308Q and identifying indicia 316Q.

FIG. 39 illustrates another embodiment of the intravenous tubing indicator 300R, which includes most of the same structural features as the intravenous tubing indicator 300A of FIGS. 24A and 24B (designated herein with an R), except for a chemotherapy haptic signature 308R and identifying indicia 316R.

FIG. 40 illustrates another embodiment of the intravenous tubing indicator 300S, which includes most of the same structural features as the intravenous tubing indicator 300A of FIGS. 24A and 24B (designated herein with a S), except for a TPN haptic signature 308S and identifying indicia 316S.

FIG. 41 illustrates another embodiment of the intravenous tubing indicator 300T, which includes most of the same structural features as the intravenous tubing indicator 300A of FIGS. 24A and 24B (designated herein with a T), except for a pediatric dosing haptic signature 308T and identifying indicia 316T.

FIG. 42 illustrates another embodiment of the intravenous tubing indicator 300V, which includes most of the same structural features as the intravenous tubing indicator 300A of FIGS. 24A and 24B (designated herein with a VP), except for a $K^+$ haptic signature 308P and potassium identifying indicia 316V.

FIG. 43 illustrates another embodiment of the intravenous tubing indicator 300W, which includes most of the same structural features as the intravenous tubing indicator 300A of FIGS. 24A and 24B (designated herein with a W), except for an obstetric haptic signature 308W and identifying indicia 316W.

Referring again to FIGS. 6 and 15, these illustrate embodiments of a "go-to line", which is the line where emergency medication is injected. The go-to line (depicted in the figures and represented herein as the "$\overline{\text{GoTo}}$ Line") must have an access port for the administration of emergency medication and it must satisfy all the requirements for the safe administration of any emergency medication.

The disclosed system employs identification tags (i.e., indicators 100 and 200) that are distributed along the $\overline{\text{GoTo}}$ Line to clearly designate the line which will always be available for the safe and secure administration of emergency IV medication.

Sometimes multiple doses of medication are injected or infused during an emergency at different times during a crisis. On many occasions after stabilizing the patient, the crisis recurs sometime later, at which time the GoTo line and other haptic indicators will still be immediately recognizable, making the line available for use. For example, multiples of a single type of medicament-specific haptic indicator (e.g., the indicator 300A of FIGS. 24A and 24B, the indicator 300B of FIGS. 25A and 25B, etc.) may remain present on a single intravenous line, indicating that such intravenous line is available for further administration of the same medicament. In some embodiments, in which such haptic indicators include twist-off tabs to indicate the number of IV bags of a medicament that have been administered to a patient, each of the multiples may have a differently numbered twist-off tab removed therefrom.

When there is an emergency, such as sudden deterioration in the patient's condition, it is necessary to find the G̅o̅T̅o̅ Line quickly and confidently. In some embodiments, a tag identifying the G̅o̅T̅o̅ line is purposefully and substantially different in appearance from other line identification tags to facilitate rapid identification.

In one embodiment, the G̅o̅T̅o̅ Line is identical to a generic infusion line except that it has three special identification tags (e.g., three instances of the indicator 100 or of the indicator 200). The tags, affixed at strategic locations along the tube, accomplish routine critical awareness of the dual role of the line: to identify and facilitate the prompt location of the line in an emergency.

In one embodiment, the locations of the tags are: (1) near the attachment spike or connector to the bag of fluid; (2) near the peristaltic pump insert or the flow rate adjusting roller clamp, and (3) near the access port at the distal end of tube, closest to the needle/catheter connection to the patient.

In one embodiment, the locations of the tags also indicate the direction of fluid flow. In one embodiment, the tags include an embossed arrow indicating the direction of fluid flow.

In another embodiment, the tags are attached to the line such that: (1) the tags will not move along the plastic tube; (2) the tags will not interfere with the use of the line to deliver fluids at specified rate and to keep the vein open; (3) the tags will not interfere with any other function involving patient care, and (4) the tags are visible.

In another embodiment, exemplary tags are packaged in a kit. In some embodiments, a kit includes at least one tag corresponding to each of at least two different medicaments (e.g., at least one of the tag 300A shown in FIGS. 24A and 24B, at least one of the tag 300B shown in FIGS. 25A and 25B, at least one of the tag 300C shown in FIGS. 26A and 26B, etc.). In some embodiments, a kit includes at least one G̅o̅T̅o̅ Line tag such as the tag 200 shown in FIGS. 14-23. In some embodiments, a kit includes at least one port cover tag such as the tag 300F shown in FIG. 29. In some embodiments a kit includes tags as described above, along with instructions for installation and use of such tags in accordance with the exemplary embodiments described herein.

For the G̅o̅T̅o̅ Line to be safe, it must only carry an acceptable fluid, such as normal saline, lactated Ringers, etc., which will not adversely affect administration of emergency medication. For the G̅o̅T̅o̅ Line to be effective, the flow must be sufficient to keep the vein open. In an embodiment, permanent, clear, unambiguous markings of the G̅o̅T̅o̅ Line keeps the G̅o̅T̅o̅ Line readily recognizable and thereby suitable and safe for subsequent use; and enables confident and timely location of the G̅o̅T̅o̅ Line when it is required in an emergency.

The proper function of the entire system relies on situation-specific design characteristics. In one embodiment, these include (1) high visibility; (2) distinctive shapes; (3) colors which assist in locating the line against drapes, equipment, bedding, etc.; (4) Low light visibility (luminescence); (5) text that provides an additional corroboration of the medicament in the IV line; (6) texture that has association with the contents of the medicament in the IV line; (7) location of tags on the IV line set (A) near the attachment spike or connector to the bag of fluid; (B) near the peristaltic pump insert or the flow rate adjusting roller clamp, and (C) near the access port at the distal end of tube, closest to the needle/catheter connection to the patient.

Example

Study Description: To evaluate the effectiveness of the exemplary embodiments in improving time to administration and accuracy of emergent bolus drug administration, a pilot study was designed using a simulated scenario replicating the conditions that typically exist in a medical transport or ICU setting (low lighting, motion, cramped quarters, complex multiple IV access sites, life sustaining infusion regimens).

Figure 44:
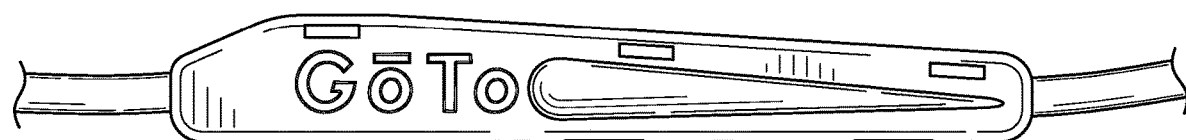
FIG. 44 is a photograph of a prototype example of an exemplary intravenous tubing indicator.

Methods: A prospective, randomized crossover study was performed in the simulation lab at the Centre for Emergency Health Sciences in Spring Branch, Tex. Study participants received a 4-minute video orientation on a tag system in accordance with the exemplary embodiments prior to beginning the study. The following scenario was then presented: The "patient" (a mannequin instrumented with a triple lumen central venous catheter, four peripheral IV catheters, a double channel IV pump, an endotracheal tube, a chest tube, a nasogastric tube to suction, and a Foley catheter) requires a STAT dose of IV midazolam to treat status epilepticus. The appropriate line to administer midazolam contains normal saline and is labeled using (in the case of the control) a standard, tape labeled IV-line or (in the case of the experiment) a tag in accordance with the exemplary embodiments. A photograph of the experimental tag in accordance with the exemplary embodiments is shown as FIG. 44. The experimental tag in accordance with the exemplary embodiments included a haptic signature that is embossed at an embossing height of 0.015 inch. The time to administration was measured by two independent observers from the time the participant entered the simulator to when the midazolam syringe content was pushed into the infusion line.

Each participant served as their own control by performing the simulation twice, in random order: once with the tape labeled IV line and once with tag in accordance with the exemplary embodiments. The simulator environment was appropriately noisy, with low lighting and a confined work space, as may be experienced in an ICU or during medical transport. To minimize learning, the appropriate infusion line was rotated systematically between the four IV sites, and ten (10) minutes separated the two simulations. Each encounter was videotaped, and an exit questionnaire captured participants' subjective impressions of the tag in accordance with the exemplary embodiments.

Subjects were dichotomized by arm and descriptive statistics were used to compare demographics between groups. Student T-tests were used to compare mean time to medication delivery, and differences between nurses, paramedics and physicians. Order bias (i.e., based on whether the tag in accordance with the exemplary embodiments was first or second in sequence) was also assessed using T-tests.

Results: For all subjects combined, the mean (+/−SD) time to administration of midazolam labeled with a tag in accordance with the exemplary embodiments (22.79±14.04 seconds) was significantly faster than the mean (+/−SD) time to administration of midazolam labeled with tape as a control (37.08±14.49 seconds; p=0.0001). Among paramedics and nurses, administration time was significantly faster statistically, whereas for physicians there was a faster administration (as indicated in Table 2 below with p>0.05). The difference was not attributable to whether the subject received the tag in accordance with the exemplary embodiments during the first or second simulation. One participant chose the incorrect line during their control/tape labeled simulation (i.e., a medication error). In the exit survey, the participants overwhelmingly concluded that the tag in accordance with the exemplary embodiments improved confidence and ease in identifying the appropriate line and that its use will improve patient safety.

TABLE 2

| Practitioner (n) | GoTo Tag (sec) | | Control (sec) | | P Value | Exemplary Tag faster # practitioners (%) | Exemplary Tag % faster (sec) |
|---|---|---|---|---|---|---|---|
| MD (4) | 26.8 | (11.9) | 35.5 | (16.5) | 0.17 | 3 (75%) | 14.6% |
| Medic (10) | 23.9 | (14.3) | 38.4 | (10.6) | <0.05 | 9 (90%) | 37.3% |
| Nurse (10) | 20.1 | (15.4) | 36.4 | (18.1) | <0.05 | 9 (90%) | 44.7% |
| Total (24) | 22.8 | (14.0) | 37.1 | (14.5) | <0.05 | 21 (88%) | 36.6% |

Conclusion: The pilot study results suggest the tag in accordance with the exemplary embodiments allows STAT drug administration to occur on average 36.6% faster than the tape labeled line.

As will be understood by those familiar with the art, the invention may be embodied in other specific forms without departing from the spirit or essential characteristics thereof. Likewise, the particular naming and division of the modules, features, attributes, methodologies, managers and other aspects are not mandatory or significant, and the mechanisms that implement the invention or its features may have different names, divisions and/or formats.

It should be emphasized that the above-described embodiments of the present disclosure are merely possible examples of implementations that are set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure.

What is claimed is:

1. A kit for expediting user recognition of intravenous tube contents, comprising:
  a first indicator, comprising a body having a first end, a second end opposite the first end, a first surface and a second surface opposite the first surface, each of which extends from the first end to the second end,
  an aperture extending from the first end to the second end, the aperture being sized and shaped to receive a first intravenous tube, and
  a first haptic signature integrally formed on at least one of the first and second surfaces,
    wherein the first haptic signature includes a first haptic and visual symbol,
    wherein the first haptic signature corresponds to the first intravenous tube contents,
    wherein the first haptic signature is configured to facilitate identification of the first intravenous tube contents when the first haptic and visual symbol is touched by a user, and
    wherein the first haptic signature is configured to facilitate identification of the first intravenous tube contents when the first haptic and visual symbol is viewed by the user; and
  a second indicator, comprising a body having a first end, a second end opposite the first end of the body of the second indicator, a first surface and a second surface opposite the first surface of the body of the second indicator, each of which extends from the first end of the body of the second indicator to the second end of the body of the second indicator,
  an aperture extending from the first end of the body of the second indicator to the second end of the body of the second indicator, the aperture being sized and shaped to receive a second intravenous tube, and
  a second haptic signature integrally formed on at least one of the first and second surfaces of the second indicator,
    wherein the second haptic signature includes a second haptic and visual symbol different from the first haptic and visual symbol,
    wherein the second haptic signature corresponds to the second intravenous tube contents,
    wherein the second haptic signature is configured to facilitate identification of the second intravenous tube contents when the second haptic and visual symbol is touched by the user, and
    wherein the second haptic signature is configured to facilitate identification of the second intravenous tube contents when the second haptic and visual symbol is viewed by the user,
  wherein each of the first indicator and the second indicator is selected from the group consisting of:
    an antihypertensive medication indicator, wherein the haptic signature of the antihypertensive medication indicator includes a first end, a second end opposite the first end of the haptic signature of the antihypertensive medication indicator, a first side having a curvilinear shape and extending from the first end of the haptic signature of the antihypertensive medication indicator to the second end of the haptic signature of the antihypertensive medication indicator, a width, and a height, wherein the width gradually decreases from the first end of the haptic signature of the antihypertensive medication indicator to the second end of the haptic signature of the antihypertensive medication indicator, and the height gradually decreases from the first end of the haptic signature of the antihypertensive medication indicator to the second end of the haptic signature of the antihypertensive medication indicator,
    an antibiotics medication indicator, wherein the haptic signature of the antibiotics medication indicator includes a first curved line portion and a second curved line portion overlapping the first curved line portion to form a loop,
    an arterial medication indicator, wherein the haptic signature of the arterial medication indicator includes a circular-shaped embossed portion and a circular-shaped indentation located within the circular-shaped embossed portion,
    a venous medication indicator, wherein the haptic signature of the venous medication indicator includes a circular-shaped debossed portion and a circular-shaped embossed portion located within the circular-shaped debossed portion, a spinal medication indicator, wherein the haptic signature of the spinal medication indicator includes a human spine-shape having plurality of vertebrae-shaped portions, an antiarrhythmics medication indicator, wherein the haptic signature of the antiarrhythmics medication indicator includes a wavelength having a first portion with at least one triangular-shaped wave and a second portion having at least one curved-shaped wave, an anticoagulant medication indicator, wherein the haptic signature of the anticoagulant medication indicator includes plurality of debossed wavy lines, a narcotics medication indicator, wherein the haptic signature of the narcotics medication indicator includes a plurality of spikes extending from the at least one of the first and second surfaces and spaced apart from one another, a blood transfusion indicator, wherein the haptic signature of the blood transfusion medication indicator includes a plurality of drop-shaped portions, each of which includes a first pointed end and a second rounded end that is wider than the first pointed end, a pressor medication indicator, wherein the haptic signature of the pressor medication indicator includes a first end, a second end opposite the first end of the haptic signature of the pressor medication indicator, a first side having a curvilinear shape and extending from the first end of the haptic signature of the pressor medication indicator to the second end of the haptic signature of the pressor medication indicator, a width, and a height, wherein the width of the haptic signature of the pressor medication indicator gradually increases from the first end of the haptic signature of the pressor medication indicator to the second end of the haptic signature of the pressor medication indicator, and the height of the haptic signature of the pressor medication indicator gradually increases from the first end of the haptic signature of the pressor medication indicator to the second end of the haptic signature of the pressor medication indicator, a paralytics medication indicator, wherein the haptic signature of the paralytics medication indicator includes a human-shaped portion having a first end, a second end opposite the first end of the human-shaped portion, and at least one channel formed therein and extending from the first end of the human-shaped portion to the second end of the human-shaped portion, an insulin medication indicator, wherein the haptic signature of the insulin medication indicator includes a grainy texture, a sedative medication indicator, wherein the haptic signature of the sedative medication indicator includes a plurality of Z-letter shaped portions, wherein the plurality of Z-letter shaped portions is oriented in a column, wherein each of the plurality of Z-letter shaped portions includes a height, wherein the height of each of the Z-letter shaped portions gradually decreases from a first one of the Z-letter shaped portions to a succeeding one of the Z-letter shaped portions, a chemotherapy medication indicator, wherein the haptic signature of the chemotherapy medication indicator includes a human head-shaped portion having a rounded first end, a TPN nutrition indicator, wherein the haptic signature of the TPN medication indicator includes a human-shaped portion having an embossed portion and debossed portion, a pediatric dosing medication indicator, wherein the haptic signature of the pediatric dosing medication indicator includes a human baby-shaped debossed portion, a potassium medication indicator, wherein the haptic signature of the potassium medication indicator includes a K-shaped embossment, an obstetrics medication indicator, wherein the haptic signature of the obstetrics medication indicator includes an embossment having a shape of a pregnant woman, and an incompatible indicator, wherein the haptic signature of the incompatible indicator includes an embossed triangle and an embossed exclamation point character within the triangle, and wherein the group of the first indicators and second indicators includes an additional medicament indicator, wherein the haptic signature of the additional medicament indicator includes an embossed text phrase GoTo, wherein text phrase is configured to identify to a user that the intravenous tube is available for administration of at least one additional medicament.

2. The kit of claim 1, wherein the body of the additional medicament indicator is green in color.

3. A system for expediting user recognition of intravenous tube contents, comprising:
   a first intravenous tube configured to carry first contents to a patient;
   a second intravenous tube configured to carry second contents to the patient, wherein the second contents is different from the first contents;
   a first indicator, comprising
   a body having a first end, a second end opposite the first end, a first surface and a second surface opposite the first surface, each of which extends from the first end to the second end,
   an aperture extending from the first end to the second end, the aperture being sized and shaped to receive the first intravenous tube, and
   a first haptic signature integrally formed on at least one of the first and second surfaces, wherein the first haptic signature includes a first haptic and visual symbol wherein the first haptic signature corresponds to the first contents, and wherein the first haptic signature is configured to facilitate identification of the first contents when the first haptic and visual symbol is touched by a user, and
   wherein the first haptic signature is configured to facilitate identification of the first contents when the first haptic and visual symbol is viewed by the user,
   wherein the first indicator is attached to the first intravenous tube; and
   a second indicator, comprising
   a body having a first end, a second end opposite the first end of the body of the second indicator, a first surface and a second surface opposite the first surface of the body of the second indicator, each of which extends from the first end of the body of the second indicator to the second end of the body of the second indicator, an aperture extending from the first end of the body of the second indicator to the second end of the body of the second indicator, the aperture of the second indicator being sized and shaped to receive the second intravenous tube, and a second haptic signature integrally formed on at least one of the first and second surfaces of the second indicator, wherein the second haptic signature includes a second haptic and visual symbol different from the first haptic and visual symbol wherein the second haptic signature corresponds to the second contents, and wherein the second haptic signature is configured to facilitate identification of the second contents when the second haptic and visual symbol is touched by the user, and wherein the second haptic signature is configured to facilitate identification of the second contents when the second haptic and visual symbol is viewed by the user, wherein the second indicator is attached to the second intravenous tube, and wherein each of the first indicator and the second indicator is selected from the group consisting of:
- an antihypertensive medication indicator, wherein the haptic signature of the antihypertensive medication indicator includes a first end, a second end opposite the first end of the haptic signature of the antihypertensive medication indicator, a first side having a curvilinear shape and extending from the first end of the haptic signature of the antihypertensive medication indicator to the second end of the haptic signature of the antihypertensive medication indicator, a width, and a height, wherein the width gradually decreases from the first end of the haptic signature of the antihypertensive medication indicator to the second end of the haptic signature of the antihypertensive medication indicator, and the height gradually decreases from the first end of the haptic signature of the antihypertensive medication indicator to the second end of the haptic signature of the antihypertensive medication indicator,
- an antibiotics medication indicator, wherein the haptic signature of the antibiotics medication indicator includes a first curved line portion and a second curved line portion overlapping the first curved line portion to form a loop,
- an arterial medication indicator, wherein the haptic signature of the arterial medication indicator includes a circular-shaped embossed portion and a circular-shaped indentation located within the circular-shaped embossed portion,
- a venous medication indicator, wherein the haptic signature of the venous medication indicator includes a circular-shaped debossed portion and a circular-shaped embossed portion located within the circular-shaped debossed portion,
- a spinal medication indicator, wherein the haptic signature of the spinal medication indicator includes a human spine-shape having plurality of vertebrae-shaped portions,
- an antiarrhythmics medication indicator, wherein the haptic signature of the antiarrhythmics medication indicator includes a wavelength having a first portion with at least one triangular-shaped wave and a second portion having at least one curved-shaped wave,
- an anticoagulant medication indicator, wherein the haptic signature of the anticoagulant medication indicator includes plurality of debossed wavy lines,
- a narcotics medication indicator, wherein the haptic signature of the narcotics medication indicator includes a plurality of spikes extending from the at least one of the first and second surfaces and spaced apart from one another,
- a blood transfusion indicator, wherein the haptic signature of the blood transfusion medication indicator includes a plurality of drop-shaped portions, each of which includes a first pointed end and a second rounded end that is wider than the first pointed end,
- a pressor medication indicator, wherein the haptic signature of the pressor medication indicator includes a first end, a second end opposite the first end of the haptic signature of the pressor medication indicator, a first side having a curvilinear shape and extending from the first end of the haptic signature of the pressor medication indicator to the second end of the haptic signature of the pressor medication indicator, a width, and a height, wherein the width of the haptic signature of the pressor medication indicator gradually increases from the first end of the haptic signature of the pressor medication indicator to the second end of the haptic signature of the pressor medication indicator, and the height of the haptic signature of the pressor medication indicator gradually increases from the first end of the haptic signature of the pressor medication indicator to the second end of the haptic signature of the pressor medication indicator,
- a paralytics medication indicator, wherein the haptic signature of the paralytics medication indicator includes a human-shaped portion having a first end, a second end opposite the first end of the human-shaped portion, and at least one channel formed therein and extending from the first end of the human-shaped portion to the second end of the human-shaped portion,
- an insulin medication indicator, wherein the haptic signature of the insulin medication indicator includes a grainy texture,
- a sedative medication indicator, wherein the haptic signature of the sedative medication indicator includes a plurality of Z-letter shaped portions, wherein the plurality of Z-letter shaped portions is oriented in a column, wherein each of the plurality of Z-letter shaped portions includes a height, wherein the height of each of the Z-letter shaped portions gradually decreases from a first one of the Z-letter shaped portions to a succeeding one of the Z-letter shaped portions,
- a chemotherapy medication indicator, wherein the haptic signature of the chemotherapy medication indicator includes a human head-shaped portion having a rounded first end,
- a TPN nutrition indicator, wherein the haptic signature of the TPN medication indicator includes a human-shaped portion having an embossed portion and debossed portion,
- a pediatric dosing medication indicator, wherein the haptic signature of the pediatric dosing medication indicator includes a human baby-shaped debossed portion,
- a potassium medication indicator, wherein the haptic signature of the potassium medication indicator includes a K-shaped embossment,
- an obstetrics medication indicator, wherein the haptic signature of the obstetrics medication indicator includes an embossment having a shape of a pregnant woman, and an incompatible indicator, wherein the haptic signature of the incompatible indicator includes an embossed triangle and an embossed exclamation point character within the triangle.

4. The system of claim 3, wherein the system includes three of the first indicators, wherein each of the three first indicators is configured to be secured at a different location along the first intravenous tube.

5. The system of claim 4, wherein a first one of the first indicators is configured to be secured to the first intravenous tube near a connector to a first bag of fluid, a second one of the first indicators is configured to be secured to the first intravenous tube near a first peristaltic pump insert or a first flow rate adjusting roller clamp, and a third one of the first indicators is configured to be secured to the first intravenous tube near a first access port at a distal end of the first intravenous tube.

6. The system of claim 5, wherein the system includes three of the second indicators, wherein each of the three second indicators is configured to be secured at a different location along the second intravenous tube.

7. The system of claim 6, wherein a first one of the second indicators is configured to be secured to the second intravenous tube near a second connector to a second bag of fluid, a second one of the second indicators is configured to be secured to the second intravenous tube near a second peristaltic pump insert or a second flow rate adjusting roller clamp, and a third one of the second indicators is configured to be secured to the second intravenous tube near a second access port at a distal end of the second intravenous tube.

8. The system of claim 3, wherein the texture of the insulin medication indicator includes a plurality of hemispherical dots having heights in a range of from 0.17 mm to 1 mm and a center-to-center spacing between adjacent dots in a range of from 1 mm to 1.5 mm.

9. The system of claim 3, wherein the texture of the insulin medication indicator includes a plurality of hemispherical dots having heights in a range of from 1 mm to 1.2 mm and a center-to-center spacing between adjacent dots in a range of that is from 1.5 mm to 2.5 mm.

10. The system of claim 3, wherein the group of the first indicators and second indicators includes an additional medicament indicator, wherein the haptic signature of the additional medicament indicator includes an embossed text phrase GoTo, wherein text phrase is configured to identify to a user that the intravenous tube is available for administration of at least one additional medicament.

11. The system of claim 10, wherein the body of the additional medicament indicator is green in color.

* * * * *